US010569092B2

(12) United States Patent
Hellman et al.

(10) Patent No.: US 10,569,092 B2
(45) Date of Patent: Feb. 25, 2020

(54) SYSTEMS AND METHODS FOR PATIENT ACTIVATED CAPTURE OF TRANSIENT DATA BY AN IMPLANTABLE MEDICAL DEVICE

(71) Applicant: PACESETTER, INC., Sylmar, CA (US)

(72) Inventors: Heidi Hellman, Los Angeles, CA (US); Joanna Urbanski, Los Angeles, CA (US); Simon Skup, Newhall, CA (US)

(73) Assignee: PACESETTER, INC., Sylmar, CA (US)

( * ) Notice: Subject to any disclaimer, the term of this patent is extended or adjusted under 35 U.S.C. 154(b) by 85 days.

(21) Appl. No.: 15/855,530

(22) Filed: Dec. 27, 2017

(65) Prior Publication Data

US 2018/0117346 A1 May 3, 2018

Related U.S. Application Data

(63) Continuation of application No. 15/233,765, filed on Aug. 10, 2016, now Pat. No. 9,889,305.

(51) Int. Cl.
*A61N 1/372* (2006.01)
*A61N 1/365* (2006.01)
*A61N 1/37* (2006.01)
*A61B 5/0402* (2006.01)

(52) U.S. Cl.
CPC ........ *A61N 1/37252* (2013.01); *A61B 5/0402* (2013.01); *A61N 1/36514* (2013.01); *A61N 1/3712* (2013.01)

(58) Field of Classification Search
None
See application file for complete search history.

(56) References Cited

U.S. PATENT DOCUMENTS

| 6,738,667 B2 | 5/2004 | Deno et al. |
| 7,096,064 B2 | 8/2006 | Deno et al. |
| 7,421,292 B1 * | 9/2008 | Kroll .................... A61N 1/3621 128/903 |

(Continued)

OTHER PUBLICATIONS

NonFinal Office Action, dated May 15, 2017—Parent U.S. Appl. No. 15/233,765.

(Continued)

*Primary Examiner* — Brian T Gedeon
(74) *Attorney, Agent, or Firm* — Dean D. Small; The Small Patent Law Group, LLC

(57) ABSTRACT

Systems and methods are provided for managing patient activated capture of transient data by an implantable medical device (IMD). The systems and methods collect transient data using the IMD. The collected transient data is stored in a temporary memory section of the IMD. The IMD receives a patient activated storage request including activation information related to a patient designated trigger point from an external device. The IMD transfers a segment of the transient data from the temporary memory section to a long-term memory, wherein the segment of transferred transient data is based on the trigger point. The activation information includes an elapsed time corresponding to a duration of time between entry of the trigger point and issuance of the patient activated storage request by an external activation device.

28 Claims, 10 Drawing Sheets

(56) References Cited

U.S. PATENT DOCUMENTS

| | | |
|---|---|---|
| 8,121,691 B2 | 2/2012 | Gerber et al. |
| 8,175,720 B2 | 5/2012 | Skelton et al. |
| 8,280,517 B2 | 10/2012 | Skelton et al. |
| 8,376,943 B2 | 2/2013 | Kovach et al. |
| 8,485,979 B2 | 7/2013 | Giftakis et al. |
| 9,529,972 B2 * | 12/2016 | Giftakis ............. A61N 1/37247 |
| 9,555,252 B2 | 1/2017 | Libbus et al. |
| 2010/0280579 A1 | 11/2010 | Denison et al. |

OTHER PUBLICATIONS

Notice of Allowance, dated Oct. 25, 2017—Parent U.S. Appl. No. 15/233,765.

* cited by examiner

SYSTEMS AND METHODS FOR PATIENT ACTIVATED CAPTURE OF TRANSIENT DATA BY AN IMPLANTABLE MEDICAL DEVICE

CROSS REFERENCE TO RELATED APPLICATIONS

This application is a continuation of U.S. patent application Ser. No. 15/233,765, filed Aug. 10, 2016.

BACKGROUND OF THE INVENTION

Embodiments of the present disclosure generally relate to systems and methods for establishing a communication link with implantable devices, and more particularly capturing and communicating data of interest between an implantable medical device and an external device.

An implantable medical device ("IMD") is a medical device that is configured to be implanted within a patient anatomy and commonly employ one or more leads with electrodes that either receive or deliver voltage, current or other electromagnetic pulses (generally "energy") from or to an organ or tissue for diagnostic or therapeutic purposes. In general, IMDs include a battery and electronic circuitry. The electronic circuitry, such as a pulse generator, and/or a microprocessor, is configured to handle RF communication with an external device. Additionally or alternatively, the electronic circuitry is configured to control patient therapy.

IMDs are programmed by, and transmit data to, external devices controlled by physicians and/or the patient. The external devices communicate through wireless communication links with the IMDs. Recently, it has been proposed that IMDs communicate with the external devices using commercial protocols, such as the Bluetooth Low Energy (BLE) protocol and other protocols which are compatible with commercial wireless devices such as tablet computers, smartphones, and the like. By enabling a commercial wireless device to communicate with the IMD using a commercial protocol, the physician and/or patient may easily and/or frequently activate communication between the IMD and the external device.

Certain conventional systems afford the patient the ability to self-activate recording of EGM data. For example, when a patient feels a symptom, the patient is able to activate communication between the external device and the IMD by means of the external device. The external device communicates to the IMD to record and store EGM data corresponding to the time at which the patient experienced a symptom. At a later time, the stored EGM data may be transmitted to a server where the EGM data is accessible to the physician. The physician may access and analyze the uploaded EGM data in order to understand the state of health of the patient.

However, the process of establishing a communication link between the IMD and the external device can be delayed. The IMD may emit advertising pulses using a wireless protocol that can be heard by other wireless devices. The advertising pulses contain information that allows a communication channel to be established between the IMD and the external devise. The advertising pulses may be emitted from the IMD on a periodic basis. In order to conserve the battery life of the IMD and to ensure a small device, the IMD advertising pulses occur at a slow rate to establish the communication channel between the IMD and the external device. The slow rate of the advertising pulses means that it could take an excessive amount of time for the IMD to establish the communication link with the external device.

After the communication link is established between the IMD and the external device, the external device may instruct the IMD to begin recording and storing transient data. However, over the course of the elapsed delay to establish the communication link, there may be transient data related to the symptom the patient has experienced that may also be of interest but that the IMD may not have recorded. The transient data of interest that occurred during the elapsed time delay establishing the communication link may be missed.

A need exists for improved methods and systems for capturing transient data and account for an elapsed delay that occurs while establishing a communication link between the IMD and the external device.

BRIEF SUMMARY

In accordance with an embodiment herein, a method is provided for managing patient activated capture of transient data by an implantable medical device (IMD). The method collects transient data using the IMD. The collected transient data is stored in a temporary memory section of the IMD. The IMD receives a patient activated (PA) storage request including activation information related to a patient designated trigger point. The IMD transfers a segment of the transient data from the temporary memory section to a long-term memory, wherein the segment of transferred transient data is based on the trigger point.

Optionally, the activation information includes an elapsed time corresponding to a duration of time between entry of the trigger point and issuance of the PA storage request. The activation information includes a patient condition indicator indicative of a condition experienced by the patient at the patient entered trigger point. The method stores the patient condition indicator with the segment of transient data. The method receives, as the trigger point, an input by a user to an external activator device. The external activator device transmits the PA storage request based on the input. The method establishes a communications link between the IMD and an external activator device.

Optionally, the method provides an application to run on an external activator device. The application identifies a trigger time stamp corresponding to a point in time when the trigger point occurs. The application identifies a connection time stamp corresponding to a point in time when a communications link is established between the IMD and the external activator device. The application calculates an elapsed time based on the trigger and connection time stamps. The elapsed time represents at least a point of the activation information. The segment of the transient data includes a starting point corresponding to the point in time when the patient entered trigger point occurred.

Optionally, the method establishes a communications session between the IMD and the external device. The communications session utilizes a wireless protocol having a connection establishment delay. The collecting operation collects electrocardiogram (EGM) data as the transient data and the transferring operation includes copying EGM data from the temporary memory section to the long term memory. The method transmits the EGM data from the IMD to the external device.

Optionally the method includes analyzing the transient data to detect a condition experienced by the patient at the patient entered trigger point and modifying therapy delivered to the patient in response to the detected condition.

In accordance with an embodiment herein, a system for capturing transient data is provided. The system includes an implantable medical device (IMD) comprising an input to collect transient data, a temporary memory section to store temporarily the transient data, a transceiver circuit to receive a patient activated (PA) storage request including activation information related to a patient designated trigger point, and a processor to transfer a segment of the transient data from the temporary memory section to a long-term memory wherein the segment is based on the trigger point.

Optionally, the system further comprises one or more sensors connected to a sensing circuit to sense cardiac signals as the transient data. The activation information includes an elapsed time corresponding to a duration of time between entry of the trigger point and a connection event at which the IMD establishes a communications link to an external activator device. The transceiver circuit is configured to establish a communications session between the IMD and an external activator device utilizing a wireless protocol having a connection establishment delay. The transceiver circuit is configured to transmit the transient data from the IMD to an external activator device.

In accordance with an embodiment herein, a system for capturing transient data is provided. The system includes an implantable medical device (IMD) comprising an input to collect transient data, a temporary memory section to store temporarily the transient data, a transceiver circuit to receive a patient activated (PA) storage request including activation information related to a patient designated trigger point, and a processor to transfer a segment of the transient data from the temporary memory section to a long-term memory wherein the segment is based on the trigger point. The system includes an external device, comprising memory storing program instructions and a processor that, when executing the program instructions, identifies a trigger point in response to a user input. The processor transmits the patient activated storage request and activation information based on the user input.

Optionally, the processor of the external activator device identifies a trigger time stamp corresponding to a point in time when the trigger point occurs. The processor identifies a connection time stamp corresponding to a point in time when a communications link is established between the IMD and the external activator device. The processor calculates an elapsed time based on the trigger and connection time stamps. The elapsed time represents at least a portion of the activation information.

Optionally, the segment of the transient data includes a starting point corresponding to the point in time when the patient entered trigger point occurred. The activation information includes a connection event time stamp represents establishment of a communications link between the IMD and an external activator device. The external activator device transmits an indication of patient condition to the IMD with the PA storage request.

DETAILED DESCRIPTION

Figure 1:
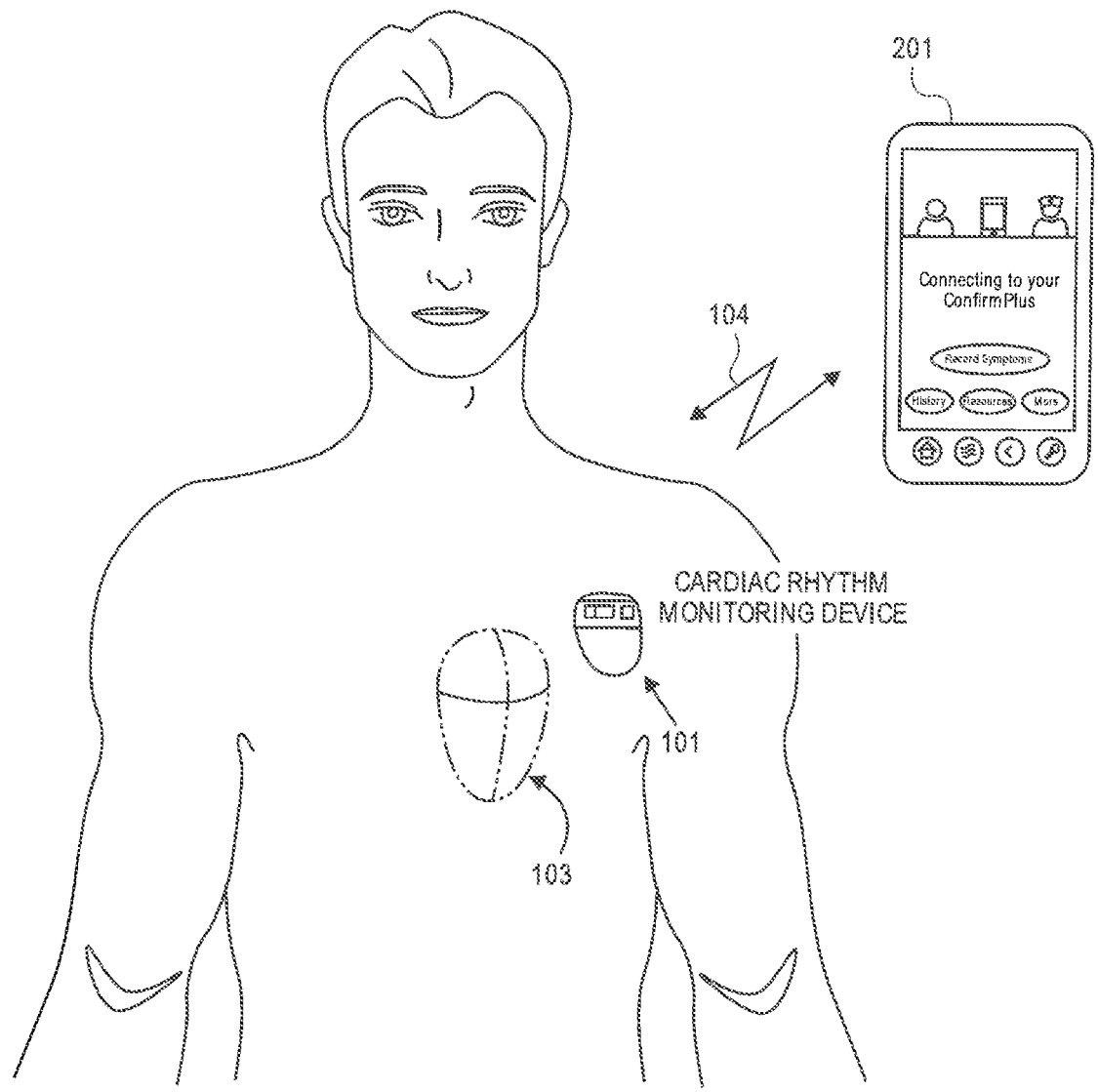
FIG. 1 illustrates a simplified block diagram of a system for initiating a bi-directional communication link according to an embodiment of the present disclosure.

While multiple embodiments are described, still other embodiments of the described subject matter will become apparent to those skilled in the art from the following detailed description and drawings, which show and describe illustrative embodiments of disclosed inventive subject matter. As will be realized, the subject matter herein is capable of modifications in various aspects, all without departing from the spirit and scope of the described subject matter. Accordingly, the drawings and detailed description are to be regarded as illustrative in nature and not restrictive.

Various embodiments described herein include a method and/or system for managing patient activated capture of transient data by an implantable medical device (IMD) using a communication link between an external device and the IMD. The IMD records transient data to a temporary memory section in a repeating, cyclical pattern, wherein once the temporary memory section is full, new transient data is recorded by overwriting the oldest transient data. For example, the temporary memory section may represent a first-in-first-out (FIFO) buffer. The IMD comprises a long-term memory section that receives transient data that is transferred from the temporary memory section. The long-term memory section stores transient data that is designated not to be overwritten.

The term "transient data" is used throughout to represent various types of data that may be recorded or logged in a temporary and/or continuous manner. Nonlimiting examples of transient data include physiologic data indicative of one or more of physiologic conditions or traits of the patient. For example, the physiologic data may represent cardiac signals sensed by electrodes positioned within or about the heart. The cardiac signals may also be sensed by electrodes provided on the housing of the IMD. As another example, the physiologic data may represent impedance signals, respiratory signals, heart sounds, nerve activity (e.g. as measured within the spinal column or dorsal root), brainwave activity and the like. The physiologic data may represent pulse oximetry signals, cholesterol related information, blood sugar levels, and the like.

Another nonlimiting example of transient data includes device related data indicative of one or more conditions or operating states of the implantable medical device. For example, the device related data may represent various types of information regarding a therapy delivered by a device, an operating condition of the device (e.g. battery life, temperature, processing power usage, errors, memory available, etc.), as well as other device status, operating state and condition information that may be of interest to log.

The external device may be a commercial wireless device (e.g. a tablet computer, a smartphone, a laptop computer). A patient, using an application on the external device, may trigger the external device to transmit signals from the external device. The transmitted signals include a connection request that the IMD establish a communications link with the external device. The application may be written to be compatible with numerous operating systems. When the connection request is detected by the IMD, the IMD enters a communication initialization mode and implements a pairing and/or bonding procedure. The pairing and/or bonding procedure may be performed based on various wireless protocols (e.g., Bluetooth Low Energy (BLE), Bluetooth, ZigBee). The pairing and/or bonding procedure may include various levels of complexity and security. For example, the procedure may include added security such as exchanging information to generate passkeys in both the IMD and the external device to establish a secure bi-directional communication link.

Once the bi-directional communication link is established, the external device communicates with the IMD for various purposes. For example, the external device sends a patient activated (PA) storage request to the IMD. The PA storage request indicates that a select portion of the transient data in the FIFO buffer should be retained long term. The PA storage request includes activation information related to a patient activated trigger point. The external device sends a PA storage request to request that the IMD transfer transient data from the temporary memory section to the long-term memory section.

The transferred transient data may be physiologic data of interest that occurred over a period of time in which the patient experienced a symptom. The transferred physiologic data will be stored in the long-term memory section so that the physiologic data may be available to a physician for review. The transferred physiologic data will allow the physician to review physiologic data corresponding to the symptom the patient experiences to understand the health of the patient.

However, the process of the patient activating the application on the external device and the external device establishing the communication link with the IMD includes an elapsed time delay. The elapsed time delay includes at least two components, namely a reaction delay and a connection establishment delay. The reaction delay corresponds to the time between when the patient determines that a symptom is being experienced and the patient is able to enter a trigger on an external device. The connection establishment delay corresponds to the time between when the user enters the trigger and the external device is able to establish a communication session with the IMD and send a PA storage request. But for the improvements described herein, a conventional IMD would record over transient data of interest (stored in the temporary memory section) that the physician may otherwise want to review. In accordance with embodiments herein, the transient data, at risk of being overwritten, is saved and transferred to long-term memory of the IMD.

The term "exposed transient data" refers to the portion of the transient data that is written to the temporary memory section for some period of time before the IMD receives a PA storage request. For example, the exposed transient data may begin at the time the patient experiences a symptom and end when the IMD receives the PA storage request. Optionally, the exposed transient data may begin some predetermined time before or after a patient experiences a symptom.

Various embodiments are described herein for identifying the elapsed time delay that has occurred before establishing the communication link with the IMD. The length of time corresponding to the elapsed time delay may be determined by the application on the external device. For example, the application may record a start trigger point when the patient activates the application. The application may record an end trigger point when the communication link is established. The time between patient activation of the application (e.g., the start trigger point) and establishing the communication link (e.g., the end trigger point) is the elapsed time delay value. Optionally, the start trigger point may be set a predetermined time before patient activation of the application.

The external device may communicate the elapsed time delay value to the IMD. The IMD uses the elapsed time delay value to identify the transient data. The transient data includes at least a component corresponding to exposed transient data (recorded before receipt of the PA storage request). Optionally, the transient data may also include a component corresponding to transient data recorded after receipt of the PA storage request. The IMD transfers the transient data corresponding to the elapsed time delay value, from the temporary memory section to be stored in the long-term memory section. For example, the PA storage request may occur at the time mark 0 minutes (e.g., the start trigger point), and the communication link is established at the time mark 5 minutes (e.g., the end trigger point). The application identifies the elapsed time delay value of 5 minutes. The external device communicates the 5 minute elapsed time delay value to the IMD. The IMD identifies the delayed transient data, temporarily stored in the temporary memory section, that corresponds to the 5 minute elapsed time delay value. The IMD transfers the delayed transient data to the long-term memory section.

Additionally or alternatively, the elapsed time delay value may be preset in the application on the external device as a preset delay value. The preset delay value may be predetermined by physician or the like. The external device may communicate the preset delay value to the IMD after the communication link is established. The IMD identifies the delayed transient data, temporarily stored in the temporary memory section, that corresponds to the preset delay value. The IMD transfers the delayed transient data, corresponding to the preset delay value, from the temporary memory section to the long-term memory section.

Various embodiments described herein may adjust the length of time corresponding to the transient data of interest based one the symptom. A symptom time value may be a predetermined value of time assigned to a symptom and stored in the memory of the external device and/or IMD. Separate symptom time values may be assigned to symptoms on a list of multiple symptoms. A unique symptom time value may be assigned to each unique symptom. Optionally, a common symptom time value may be assigned to a set of symptoms on the list of multiple symptoms. The symptom time value may be a predetermined length of time configured by a physician, or the like.

The list of symptoms may represent a list of identifiable symptoms that the patient may experience and that relate to the health of the patient. The list of symptoms may be a predetermined list configured by a physician, or the like. For example, the list of symptoms may include fainting, fast heartbeat, heart flutter, dizziness, chest pain, and the like. For example, the symptom time value assigned to fainting may be 12 minutes, and the symptom time value assigned to fast heartbeat may be 16 minutes. The patient may select a symptom from the list of symptoms using the application on the external device.

The selected symptom and the corresponding symptom time value assigned to the selected symptom may be communicated to the IMD. The transient data that occurs over the length of time corresponding to the symptom time value may also be referred to as symptom physiologic data. The IMD uses the symptom time value to identify the symptom physiologic data. The IMD may transfer the symptom physiologic data, corresponding to the symptom time value, from the temporary memory section to the long-term memory section. For example, the patient may select the symptom fast heartbeat from the list of symptoms. The symptom time value assigned to the fast heartbeat symptom may be 16 minutes. The external device may communicate the fast heartbeat symptom and 16 minute symptom time value to the IMD. The IMD identifies the symptom physiologic data, temporarily stored in the temporary memory section, that corresponds to the 16 minute symptom time value. The IMD transfers the symptom transient data to the long-term memory section.

A technical effect of the various embodiments herein is to facilitate recording, in long-term memory, of transient data of interest that is temporally concurrent with the moment that the patient is experiencing a symptom even though a patient reaction delay and a connection establishment delay occur between the point in time when a patient experiences a symptom and the external device establishes a communications session with the IMD. A technical effect of recording the transient data of interest is to provide the physician with recorded transient data that aligns with the symptom at the moment in time that the patient is experiencing the symptom. A technical effect of various embodiments herein is to increase the amount of transient data contemporaneous with symptoms and episodes, that is provided to the physician for analysis to better understand the overall health of the patient.

FIG. 1 illustrates a simplified block diagram of a system for establishing a communication link between an external activator device 201 and an implantable medical device (IMD) 101. The external activator device 201 may represent a tablet computer, smartphone, laptop, or the like. The external activator device 201 may program the IMD 101 and/or receive data from the IMD 101 via a communication link 104. For example, the external activator device 201 may transmit a request to the IMD 101. The request is received by the IMD 101, and in response to the request, the IMD 101 may transfer transient data from a temporary memory section of the IMD 101 to a long-term memory section of the IMD 101. The communication link 104 may use any standard wireless protocol such as a Bluetooth Low Energy (BLE) protocol, Bluetooth protocol, Wireless USB protocol, Medical Implant Communication Service (MISC) protocol, ZigBee protocol, and/or the like that define a means for transmitting and receiving information (e.g., data, commands, instructions) between devices. Optionally, the communications link 104 may use any protocol that experiences a connection establishment delay between i) the time a user activates an input indicative of a desire to convey a request to an IMD and ii) the time that the request is transmitted.

The IMD 101 may be implanted within a patient 106 (e.g., proximate to a heart 103, proximate to the spinal cord). Additionally or alternatively, the IMD 101 may have components that are external to the patient 106, for example, the IMD 101 may constitute a neuro external pulse generator (EPG). The IMD 101 may be one of various types of implantable devices, such as, for example, an implantable cardiac monitoring device (ICM), a leadless pacemaker, neurostimulator, electrophysiology (EP) mapping and radio frequency (RF) ablation system, an implantable pacemaker, implantable cardioverter-defibrillator (ICD), defibrillator, cardiac rhythm management (CRM) device, an implantable pulse generator (IPG), or the like.

Figure 2:
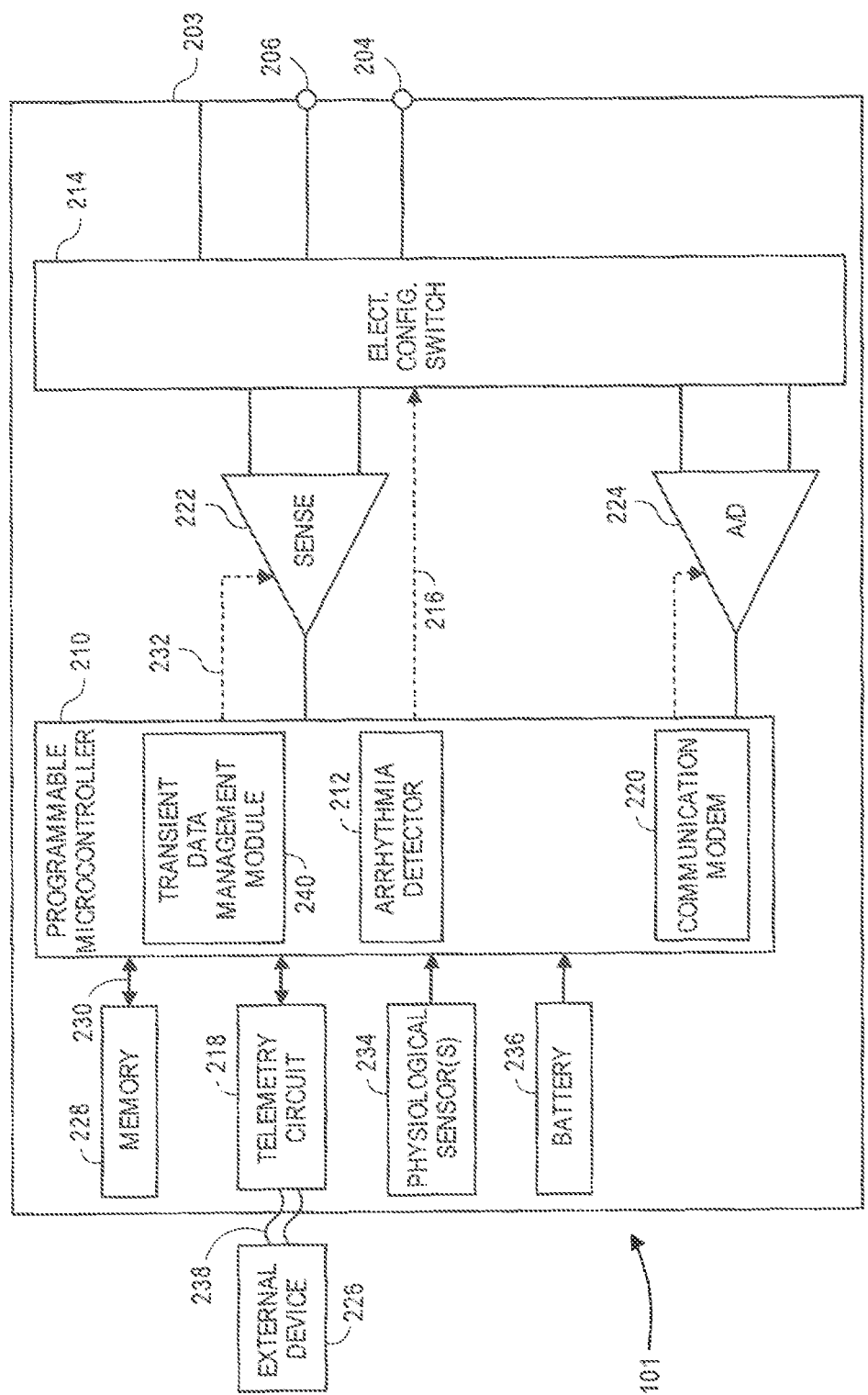
FIG. 2 illustrates a block diagram of the internal components of an implantable medical device according to an embodiment of the present disclosure.

FIG. 2 illustrates a block diagram of an exemplary IMD 101 that is configured to be implanted into the patient. The systems described herein can include or represent hardware and associated instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. These devices may be off-the-shelf devices that perform the operations described herein from the instructions described above. Additionally or alternatively, one or more of these devices may be hard-wired with logic circuits to perform these operations.

The IMD 101 is configured to collect one or more types of transient data, which may include physiologic data and/or device related data. For example, in connection with collecting physiologic data, the IMD 101 may be implemented to monitor ventricular activity alone, or both ventricular and atrial activity through sensing circuitry. Additionally or alternatively, the IMD 101 may monitor respiratory activity, heart sounds, diabetes related physiologic information, cholesterol, impedance, nerve fiber activity, brainwave activity and the like. The IMD 101 has a housing 203 to hold the electronic/computing components. The housing 203 (which is often referred to as the "can", "case", "encasing", or "case electrode") may be programmably selected to act as an electrode for certain sensing modes. Housing 203 further includes a connector (not shown) with at least one terminal 206 and preferably a second terminal 204. The terminals 206, 204 may be coupled to sensing electrodes (on the device housing, in the header, or located otherwise) that are provided upon or immediately adjacent the housing 203. Additionally or alternatively, the terminals 206, 204 may be connected to one or more leads having one or more electrodes provided thereon, where the electrodes are located in various locations about the heart. The type and location of each electrode may vary.

The IMD 101 is configured to be placed subcutaneously utilizing a minimally invasive approach. Subcutaneous electrodes are provided on the housing 203 to simplify the implant procedure and eliminate a need for a transvenous lead system. The sensing electrodes may be located on opposite sides/ends of the device and designed to provide robust episode detection through consistent contact at a sensor-tissue interface. The IMD 101 may be configured to be activated by the patient or automatically activated, in connection with recording transient data.

The IMD 101 includes a programmable microcontroller 210 that controls various operations of the IMD 101, including physiologic data monitoring and/or device related data logging. Microcontroller 210 includes a microprocessor (or equivalent control circuitry), RAM and/or ROM memory, logic and timing circuitry, state machine circuitry, and I/O circuitry. As one example of physiologic data, the microcontroller 210 performs the operations in connection with collecting cardiac activity data and analyzing the cardiac activity data to identify episodes of interest. As one example of a technique for analyzing cardiac activity, the microcontroller 210 includes an arrhythmia detector 212 that is configured to analyze cardiac activity data to identify potential AF episodes as well as other arrhythmias (e.g. Tachycardias, Bradycardias, Asystole, etc.).

The microcontroller 210 performs the operations in connection with collecting device related data. The microcontroller 210 may periodically run a self-diagnostic check for a status of the IMD 101. For example, the microcontroller 210 may run a self-diagnostic check to verify the device is operating correctly every 24 hours. Optionally, the microcontroller 210 may run a self-diagnostic check when a command is communicated by a patient, physician, and the like. The device related data may represent various types of information regarding a therapy delivered by the IMD 101, an operating condition of the IMD (e.g., battery life, temperature, processing power usage, errors, memory available, etc.), as well as other device status, operating state, and condition information that may be of interest to log. For example, the microcontroller 210 may run a self-diagnostic check and identify that the battery life of the IMD 101 is nearing expiration. The microcontroller may identify the transient data (e.g., the device related data of the battery life of the IMD) to be device related data of interest.

The programmable microcontroller 210 further includes a transient data management module 240. The transient data management module 240 may include programmed software/firmware that identifies transient data of interest from the collected transient data. The identified transient data of interest may include physiologic data and/or device related data of interest. For example, the microcontroller 210 collects cardiac activity data as transient data. The transient data management module 240 identifies a segment of the cardiac activity data as transient data of interest. The transient data management module 240 may be configured to select the transient data of interest and identify the transient data of interest as persistent data to be stored in a long-term memory section.

In accordance with certain embodiments, the electrodes may be directly coupled to sensing circuits in a predetermined hardwired electrode configuration. Alternatively, a switch 214 may be provided, where the switch 214 is managed by the microcontroller 210 select different electrode configurations. The switch 214 is controlled by a control signal 216 from the microcontroller 210. Optionally, the switch 214 may be omitted and the circuits directly connected to the housing electrode and a second electrode.

The IMD 101 is further equipped with a telemetry circuit 218 and a communication modem (modulator/demodulator) 220 to enable wireless communication. In one implementation, the telemetry circuit 218 and communication modem 220 use high frequency modulation, for example using RF or Blue Tooth telemetry protocols. The telemetry circuit 218 may include one or more transceivers. For example, the telemetry circuit 218 may be coupled to an antenna in the header that transmits communications signals in a high frequency range that will travel through the body tissue in fluids without stimulating the heart or being felt by the patient. The communication modem 220 may be implemented in hardware as part of the microcontroller 210, or as software/firmware instructions programmed into and executed by the microcontroller 210.

The IMD 101 includes sensing circuitry 222 selectively coupled to one or more electrodes that perform sensing operations, through the switch 214 to detect physiologic data indicative of physiologic activity of interest. The sensing circuitry 222 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the physiologic activity of interest. In one embodiment, switch 214 may be used to determine the sensing polarity of the physiologic signal by selectively closing the appropriate switches.

The output of the sensing circuitry 222 is connected to the microcontroller 210 which, in turn, determines when to store the physiologic activity data (digitized by the A/D data acquisition system 224) in the memory 228. The sensing circuitry 222 receives a control signal 232 from the microcontroller 210 for purposes of controlling the gain, threshold, polarization charge removal circuitry (not shown), and the timing of any blocking circuitry (not shown) coupled to the inputs of the sensing circuitry.

By way of example, the external device 226 may represent a portable electronic device (e.g. smart phone, iPad, laptop computer, smart watch, wearable wristband, bedside monitor installed in a patient's home, etc.) and utilized to communicate with the IMD 101 while the patient is at home, in bed or asleep. The external device 226 may be a programmer used in the clinic to interrogate the device, retrieve data and program detection criteria and other features. The external device 226 may be a device that can be coupled over a network (e.g. the Internet) to a remote monitoring service, medical network and the like. The external device 226 facilitates access by physicians to patient data as well as permitting the physician to review real-time ECG signals while being collected by the IMD 101.

The microcontroller 210 is coupled to a memory 228 by a suitable data/address bus 230. The programmable operating parameters used by the microcontroller 210 are stored in memory 228 and used to customize the operation of the IMD 101 to suit the needs of a particular patient. Such operating parameters define, for example, detection rate thresholds, sensitivity, automatic features, arrhythmia detection criteria, activity sensing or other physiological sensors, and electrode polarity, etc. The operating parameters of the IMD 101 may be non-invasively programmed into the memory 228 through a telemetry circuit 218 in telemetric communication via communication link 238 with the external device 226. The telemetry circuit 218 allows intracardiac electrograms and status information relating to the operation of the IMD 101 (as contained in the microcontroller 210 or memory 228) to be sent to the external device 226 through the established communication link 238. The IMD 101 may further include magnet detection circuitry (not shown), coupled to the microcontroller 210, to detect when a magnet is placed over the unit. A magnet may be used by a clinician to perform various test functions of the unit 200 and/or to signal the microcontroller 210 that the external device 226 is in place to receive or transmit data to the microcontroller 210 through the telemetry circuits 218. The IMD 101 can further include one or more physiologic sensor 234. Such sensors are commonly referred to (in the pacemaker arts) as "rate-responsive" or "exercise" sensors. The physiological sensor 234 may further be used to detect changes in the physiological condition of the heart, or diurnal changes in activity (e.g., detecting sleep and wake states). Signals generated by the physiological sensors 234 are passed to the microcontroller 210 for analysis and optional storage in the memory 228 in connection with the cardiac activity data, markers, episode information and the like. While shown as being included within the device 200, the physiologic sensor (s) 234 may be external to the device 200, yet still be implanted within or carried by the patient. Examples of physiologic sensors might include sensors that, for example, activity, temperature, sense respiration rate, pH of blood, ventricular gradient, activity, position/posture, minute ventilation (MV), and so forth.

A battery 236 provides operating power to all of the components in the IMD 101. The battery 236 is capable of operating at low current drains for long periods of time. The battery 236 also desirably has a predictable discharge characteristic so that elective replacement time can be detected. As one example, the device 200 employs lithium/silver vanadium oxide batteries. The battery 236 may afford various periods of longevity (e.g. three years or more of device monitoring). In alternate embodiments, the batter 236 could be rechargeable. See for example, U.S. Pat. No. 7,294,108, Cardiac event microrecorder and method for implanting same, which is hereby incorporated by reference.

Figure 6:
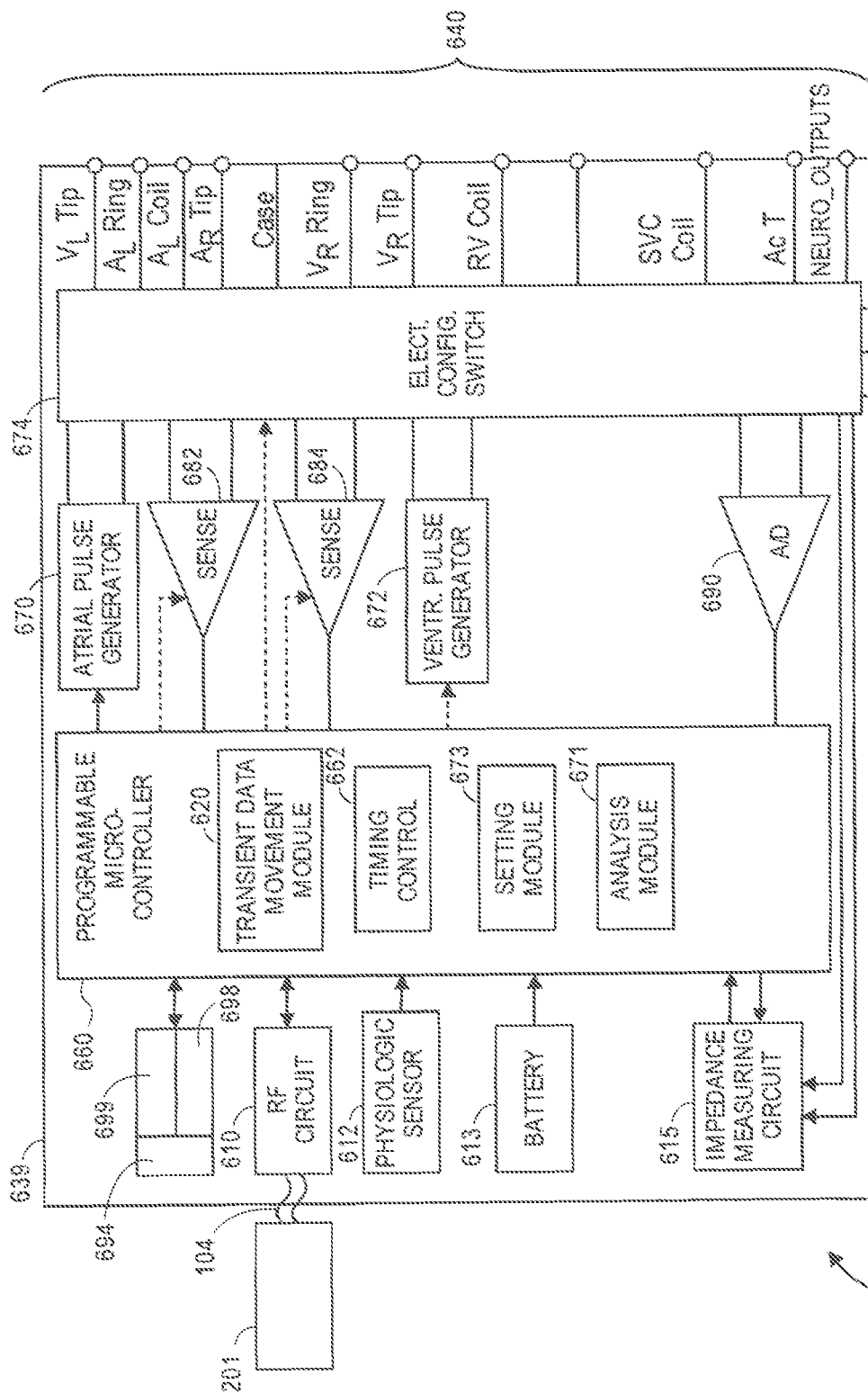
FIG. 6 illustrates a block diagram of the internal components of an implantable medical device according to an embodiment of the present disclosure.

FIG. 6 illustrates a block diagram of internal components of the IMD 101. The IMD 101 is for illustration purposes only, and it is understood that the circuitry could be duplicated, eliminated or disabled in any desired combination to provide a device capable of treating the appropriate chamber (s) with cardioversion, defibrillation and/or pacing stimulation as well as providing for apnea detection and therapy. A housing 639 for the IMD 101, shown schematically in FIG. 6, is often referred to as the "can", "case" or "case electrode" and may be programmably selected to act as the return electrode for all "unipolar" modes. The housing 639 may further be used as a return electrode alone or in combination with one or more of the coil electrodes for shocking purposes. The housing 639 further includes a connector (not shown) having a plurality of terminals 640 (shown schematically). For convenience, the names of the electrodes are shown next to the terminals. Optionally, the terminals may include an acoustic terminal (ACT) adapted to be connected to an external acoustic sensor or an internal acoustic sensor, depending upon which (if any) acoustic sensors are used. Optionally, the terminals may include a terminal adapted to be connected to a blood sensor to collect measurements associated with glucose levels, natriuretic peptide levels, or catecholamine levels. Optionally, the terminals 640 may include one or more terminals adapted to be connected to nerve fiber sensors.

The IMD 101 includes a programmable microcontroller 660 which controls operations. The microcontroller 660 (also referred to herein as a processor module or unit) typically includes a one or more processors or microprocessors, or equivalent control circuitry, designed specifically for controlling the delivery of stimulation therapy and may further include RAM or ROM memory, logic, timing circuitry, state machine circuitry, and I/O circuitry. Typically, the microcontroller 660 includes the ability to process or monitor input signals (data) as controlled by program code stored in memory. The details of the design and operation of the microcontroller 660 are not critical to the embodiments described herein. Rather, any suitable microcontroller 660 may be used that carries out the functions described herein. Among other things, the microcontroller 660 receives, processes, and manages storage of digitized transient data sets from the various sensors and electrodes. For example, the transient data sets may include physiologic data such as EGM data, pressure data, heart sound data, and the like. Additionally or alternatively, the transient data sets may include device related data such as therapy delivery, battery life, available memory, device errors, and the like.

The microcontroller 660 includes the ability to perform the operations of collecting device related data. The microcontroller 660 may periodically run a self-diagnostic check for a status of the IMD 101. For example, the microcontroller 660 may run a self-diagnostic check to verify the device is operating correctly. The device related data may represent various types of information regarding a therapy delivered by the IMD 101, an operating condition of the IMD, as well as other device status, operating state, and condition information that may be of interest to log. For example, the microcontroller 660 may run a self-diagnostic check every 24-hours and identify that the battery life of the IMD 101 is nearing expiration. Optionally, the microcontroller 660 may run a self-diagnostic check when a check command is communicated to the IMD 101 by a patient, physician, and the like. The microcontroller may identify the transient data (e.g., the device related data of the battery life of the IMD) to be logged as device related data of interest.

The IMD 101 includes one or more pulse generators 670, 672 to generate pacing stimulation pulses for delivery to electrodes via an electrode configuration switch 674. The pulse generators, 670 and 672, may include dedicated, independent pulse generators, multiplexed pulse generators or shared pulse generators. The pulse generators, 670 and 672, are controlled by the microcontroller 660 via appropriate control signals to trigger or inhibit the stimulation pulses. As one example, the pulse generators 670, 672 may generate atrial and ventricular pacing pulses, cardioversion therapy, defibrillation shocks and the like. Optionally, the IMD 101 may represent a neuro stimulation device, in which case the pulse generators 670, 672 represent neuro pulse generators to generate stimulation pulses for a brain or spinal cord nervous system. In this alternatively embodiment, the stimulation pulses are delivered by a plurality of electrodes through a neuro-stimulation lead.

The microcontroller 660 further includes timing control circuitry 662 used to control the timing of stimulation pulses (e.g., pacing rate, atria-ventricular (AV) delay, atrial interconduction (A-A) delay, or ventricular interconduction (V-V) delay, neurostimulation therapy, brainwave therapy, etc.). Optionally, the control circuitry 662 monitors the timing of the physiologic characteristics of interest, such as refractory periods, blanking intervals, noise detection windows, evoked response windows, alert intervals, marker channel timing, and the like. Switch 674 includes a plurality of switches for connecting the desired electrodes to the appropriate I/O circuits, thereby providing complete electrode programmability. Accordingly, the switch 674, in response to a control signal from the microcontroller 660, determines the polarity of the stimulation pulses (e.g., unipolar, bipolar, etc.) by selectively closing the appropriate combination of switches (not shown) as is known in the art.

Sensing circuits 682, 684 are selectively coupled to the leads and/or electrodes through the terminals 640 and switch 674. The sensing circuits are configured to detect various physiologic characteristics of interest and generate physiologic data indicative of the physiologic characteristics. At least a portion of the physiologic data is then stored as transient data in memory 694. The sensing circuits 682, 684, may include dedicated sense amplifiers, multiplexed amplifiers or shared amplifiers. When implemented in connection with a pacemaker, cardioverter and/or defibrillator, the outputs of the sensing circuits, 682 and 684, are connected to the microcontroller 660 and are used to trigger or inhibit generation of atrial and ventricular pulses, respectively, in a demand fashion in response to the absence or presence of cardiac activity in the appropriate chambers of the heart.

Physiologic signals are also applied to the inputs of an analog-to-digital (A/D) data acquisition system 690. For example, the data acquisition system 690 is configured to acquire physiologic data signals, convert the raw analog data into a digital physiologic signal, and store the digital physiologic data in memory 694 for later processing and/or RF transmission. At least a portion of the digital physiologic data is transient data that is saved in a temporary memory section of the memory 694 and processed as explained herein. The data acquisition system 690 is coupled to one or more electrodes and leads through the switch 674 to sample cardiac signals across any combination of desired electrodes. The data acquisition system 690 may also be coupled, through switch 674, to one or more other types of sensors such as acoustic sensors. The data acquisition system 690 may also acquire, performs A/D conversion, produce and save digital pressure data, acoustic data, and the like.

The microcontroller 660 includes an analysis module 671 and a setting module 673 that function in accordance with embodiments described herein. When implemented in a pacemaker, the analysis module 671 analyzes a characteristic of interest from the heart. The level of the characteristic changes as the pacing parameter is changed. The setting module 673 sets a desired value for the pacing parameter based on the characteristic of interest from the heart. The pacing parameter may represent at least one of an AV delay, a VV delay, a VA delay, intra-ventricular delays, electrode configurations and the like. The microcontroller 660 changes at least one of the AV delay, the VV delay, the VA delay, the intra-ventricular delays, electrode configurations and like in order to reduce systolic turbulence and regurgitation.

An RF circuit 610 is configured to handle and/or manage the communication link 104 between the IMD 101 and the external activator device 201. The RF circuit 610 is electrically coupled to the microcontroller 660, and is controlled by the microcontroller 660 and may support a particular wireless communication protocol while communicating with the external activator device 101, such as BLE, Bluetooth, ZigBee, Medical Implant Communication Service (MICS), or the like. Protocol firmware may be stored in memory 694, which is accessed by the microcontroller 660. The protocol firmware provides the wireless protocol syntax for the microcontroller 660 to assemble data packets, establish communication links 104, and/or partition data received from the external activator device 201.

The microcontroller 660 is electrically coupled to the memory 694 by a suitable data/address bus, wherein the programmable operating parameters used by the microcontroller 660 are stored and modified, as required, in order to customize the operation of IMD 101 to suit the needs of a particular patient. The memory 694 may be a non-transitory computer readable medium such as RAM, ROM, EEPROM, a hard drive, or the like.

The memory 694 comprises a temporary memory section 699 and a long-term memory section 698. The temporary memory section 699 records and temporarily stores data sets (raw data, summary data, histograms, etc.), such as the EGM data, heart sound data, pressure data, Sv02 data and the like for a desired period of time (e.g., 30 minutes, 2 hour, 24 hours). The temporary memory section 699 may be configured to continuously cyclically record and temporarily store transient data for a predetermined length of time (e.g., 30 minutes), wherein once the temporary memory section 699 is full, new transient data is recorded by overwriting the oldest transient data. For example, the temporary memory section 699 records EGM data and temporarily stores the recorded data until the temporary memory section is full. The temporary memory section 699 then records and temporarily stores new EGM data by overwriting the oldest transient data as a first-in-first-out (FIFO) continuous buffer.

The microcontroller 660 further includes a transient data management module 620. The transient data management module 620 may include programmed software/firmware that selects transient data from the data temporarily stored in the temporary memory section 699 that is of interest. The transient data management module 620 instructs the temporary memory section 699 to transfer transient data of interest to the long-term memory section 698 of the memory 694. The long-term memory section 698 stores the transferred transient data of interest for a preconfigured period of time (e.g., 2 hour, 24 hours, 2 month). The transient data of interest stored in the long-term memory section 698 may be available to a physician or the like. Additionally or alternatively, the temporary memory section 699 and the long-term memory section 698 may be individual components within the IMD 101. Details related identifying and transferring transient data from the temporary memory section 699 to the long-term memory section 698 will be described later herein.

The pacing and other operating parameters of the IMD 101 may be non-invasively programmed into the memory 694 through the RF circuit 610 via the communication link 104. The RF circuit 610 is controlled by the microcontroller 660 and receives data for transmission by an interconnect. The RF circuit 610 allows various types of transient and persistent data (e.g., intra-cardiac electrograms, pressure data, acoustic data, Sv02 data, and status information relating to the operation of IMD 101 as contained in the microcontroller 660 or memory 694) to be sent to the external activator device 201 through the established communication link 205. The RF circuit 610 also allows new pacing parameters for the setting module 673 used by the IMD 101 to be programmed through the communication link 104.

To establish the communication link 104 between the external activator device 201 and the IMD 101, the microcontroller 660 may enter an advertisement mode by instructing the RF circuit 610 to transmit or broadcast one or more advertisement notices along a dedicated advertisement channel defined by the wireless protocol. The advertisement channel is a point to multipoint, unidirectional, channel to carry a repeating pattern of system information messages such as network identification, allowable RF channels to establish the communication link 205, and/or the like that is included within the advertisement notice. The advertisement notice may be repeatedly transmitted after a set duration or an advertisement period until the communication link 104 is established with the external activator device 201.

Optionally, the length of the advertisement period may be adjusted by the microcontroller 660 during a select advertisement mode. For example, during the select advertisement mode the microcontroller 660 may reduce the length of the advertisement period relative to not being in the select advertisement mode. The reduced length of the advertisement period results in the RF circuit 610 transmitting more or an increased number of advertisement notices relative to not being in the select advertisement mode.

Optionally, the external activator device 201 may establish the communication link 104 with the IMD 101 by using a wireless protocol with a predetermined connection time schedule. For example, the predetermined connection time schedule may include a predetermined delay time of 30 seconds required to establish a communication link between the IMD 101 and the external activator device 201.

The IMD 101 may also include a physiologic sensor 612, such as an accelerometer, commonly referred to as a "rate-responsive" sensor, to record the activity level of the patient or adjust pacing stimulation rate according to the exercise state of the patient. Optionally, the physiological sensor 612 may further be used to detect changes in cardiac output, changes in the physiological condition of the heart, or changes in activity (e.g., detecting sleep and wake states) and movement positions of the patient. While shown as being included within IMD 101, it is to be understood that the physiologic sensor 612 may also be external to the IMD 101, yet still be implanted within or carried by the patient. A common type of rate responsive sensor is an activity sensor incorporating an accelerometer or a piezoelectric crystal, which is mounted within the housing 639 of the IMD 101.

The physiologic sensor 612 may be used as the acoustic sensor that is configured to detect the heart sounds. For example, the physiologic sensor 612 may be an accelerometer that is operated to detect acoustic waves produced by blood turbulence and vibration of the cardiac structures within the heart (e.g., valve movement, contraction and relaxation of chamber walls and the like). When the physiologic sensor 612 operates as the acoustic sensor, it may supplement or replace entirely acoustic sensors. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient and, in particular, is capable of detecting arousal from sleep or other movement.

The IMD 101 additionally includes a battery 613, which provides operating power to all of the circuits shown. The IMD 101 is shown as having impedance measuring circuit 615 which is enabled by the microcontroller 660. Herein, impedance is primarily detected for use in evaluating ventricular end diastolic volume (EDV) but is also used to track respiration cycles. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 615 is advantageously coupled to the switch 674 so that impedance at any desired electrode may be obtained.

Figure 3:
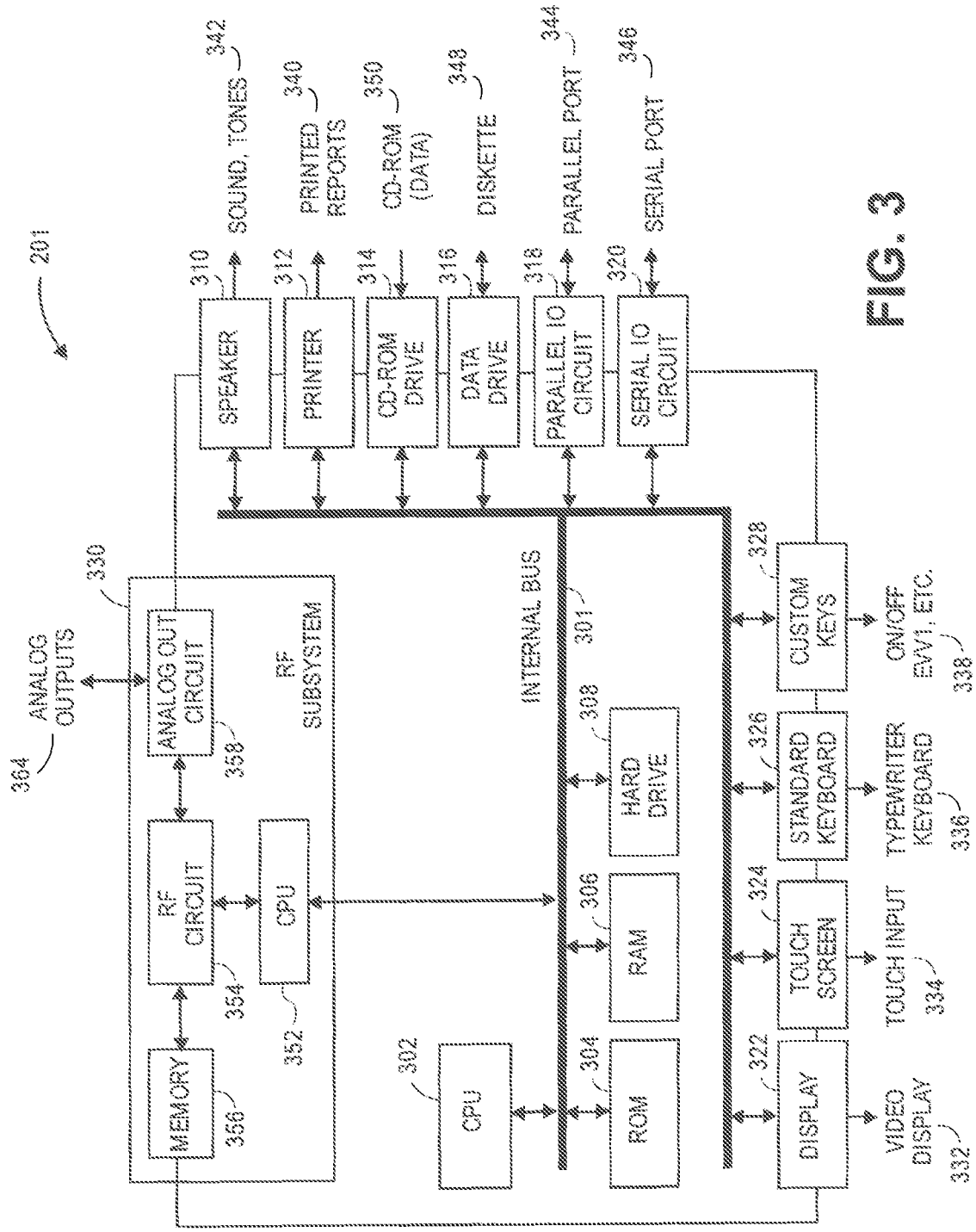
FIG. 3 illustrates a block diagram of internal components of an external device according to an embodiment of the present disclosure.

FIG. 3 illustrates a functional block diagram of the external activator device 201 that is operated in accordance with the processes described herein and to interface with the IMD 101 as described herein. The external activator device 201 may be an off-the-shelf device that performs the operations described herein from the instructions described above. Additionally or alternatively, the device may be hard-wired with logic circuits to perform these operations. For example, the external activator device 201 may be a tablet computer, a smartphone, a laptop computer, a workstation, an IMD programmer, a PDA and/or the like located within a home of the patient 106, a hospital or clinic, an automobile, at an office of the patient, or the like. The external activator device 201 is for illustration purposes only, and it is understood that the circuitry could be duplicated, eliminated or disabled in any desired combination to provide a device capable of communicating with the IMD 101.

The external activator device 201 may include an internal bus 301 that may connect/interface with a Central Processing Unit ("CPU") 302, ROM 304, RAM 306, a hard drive 308, a speaker 310, a printer 312, a CD-ROM drive 314, a floppy drive 316, a parallel I/O circuit 318, a serial I/O circuit 320, a display 322, a touchscreen 324, a standard keyboard 326, custom keys 328, and an RF subsystem 330. The internal bus 301 is an address/data bus that transfers information between the various components described herein. The hard drive 308 may store operational programs as well as data, such as stimulation waveform templates and detection thresholds.

The CPU 302 typically includes a microprocessor, a micro-controller, or equivalent control circuitry, designed specifically to control interfacing with the external activator device 201 and with the IMD 101. The CPU 302 may include RAM or ROM memory, logic and timing circuitry, state machine circuitry, and I/O circuitry to interface with the IMD 101. The display 322 (e.g., may be connected to a video display 332). The display 322 displays various information related to the processes described herein. The touchscreen 324 may display graphic information relating to the IMD 101 and include a graphical user interface. The graphical user interface may include graphical icons, scroll bars, buttons, and the like which may receive or detect user or touch inputs 334 for the external activator device 201 when selections are made by the user. Optionally the touchscreen 324 may be integrated with the display 322. The keyboard 326 (e.g., a typewriter keyboard 336) allows the user to enter data to the displayed fields, as well as interface with the RF subsystem 330. Furthermore, custom keys 328 turn on/off 338 (e.g., EVVI) the external activator device 201. The printer 312 prints copies of reports 340 for a physician to review or to be placed in a patient file, and the speaker 310 provides an audible warning (e.g., sounds and tones 342) to the user. The parallel I/O circuit 318 interfaces with a parallel port 344. The serial I/O circuit 320 interfaces with a serial port 346. The floppy drive 316 accepts diskettes 348. Optionally, the serial I/O port may be coupled to a USB port or other interface capable of communicating with a USB device such as a memory stick. The CD-ROM drive 314 accepts CD ROMs 350.

The RF subsystem 330 includes a central processing unit (CPU) 352 in electrical communication with an RF circuit 354, which may communicate with both memory 356 and an analog out circuit 358. The analog out circuit 358 includes communication circuits to communicate with analog outputs 364. The external activator device 201 may wirelessly communicate with the IMD 101 and utilize protocols, such as Bluetooth, BLE, ZigBee, MICS, and the like.

The microcontroller 660 (of FIG. 6), the CPU 302, and the CPU 352 may execute a set of instructions that are stored in one or more storage elements, in order to process data. The storage elements may also store data or other information as desired or needed. The storage element may be in the form of an information source or a physical memory element within the microcontroller 660, the CPU 302, and the CPU 352. The set of instructions may include various commands that instruct the microcontroller 660, the CPU 302, and the CPU 352 to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine. For example, the external activator device 201 may be equipped with at least one of an application software that is available for patient interaction through a graphical icon on the touchscreen 324. The application software may be programmed to initiate the external activator device 201 to request the communication link 104 between the external activator device 201 and the IMD 101 at the command of the patient.

Figure 4:
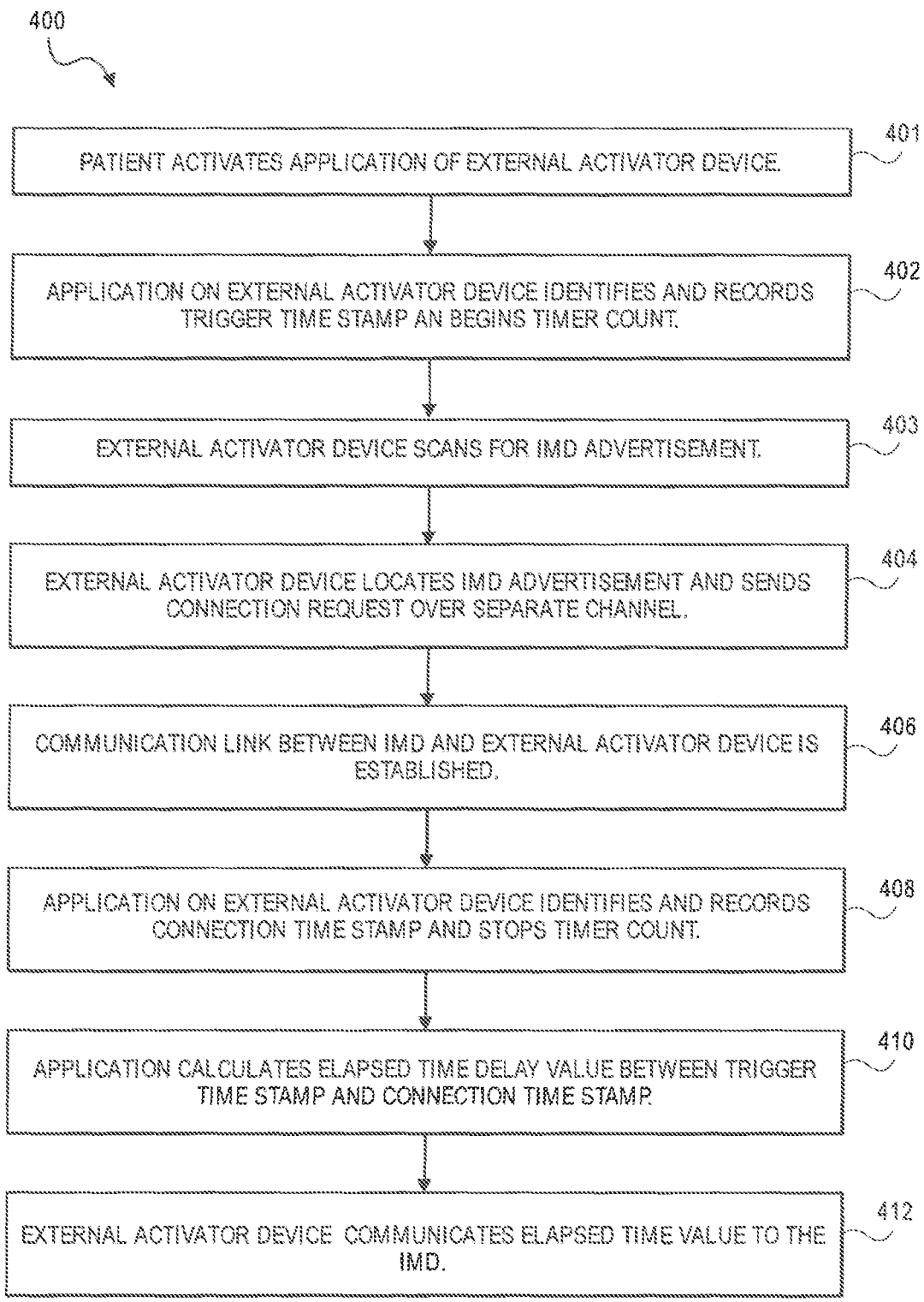
FIG. 4 illustrates a flowchart of a method for establishing a communication link between an external device and an implantable medical device according to an embodiment of the present disclosure.
Figure 5:
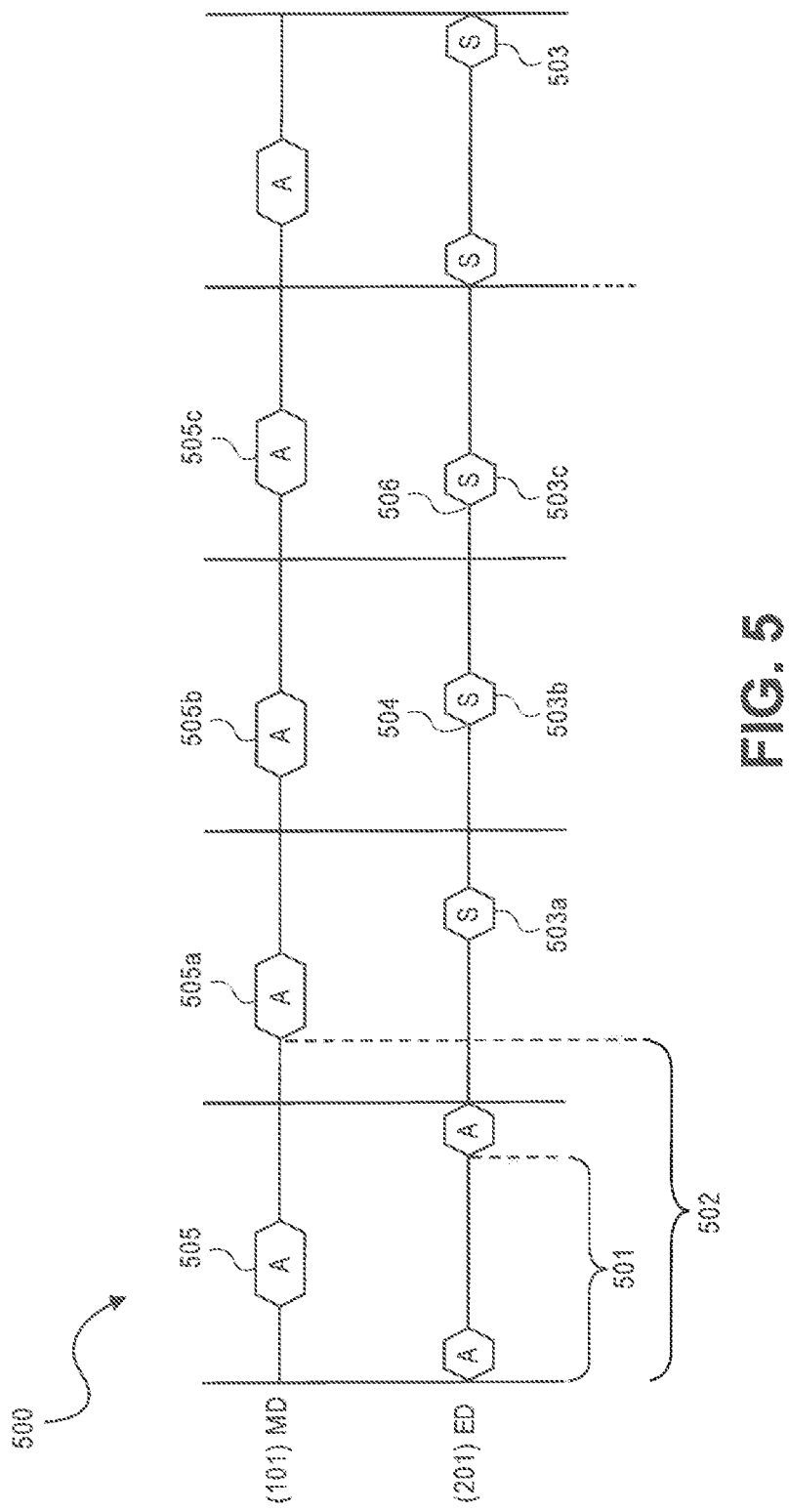
FIG. 5 illustrates a timing diagram of transmissions between an external device and an implantable medical device according to an embodiment of the present disclosure.

FIG. 4 illustrates a flowchart of a method 400 for establishing a communication link between an external activator device (e.g., 201) and an implantable medical device (IMD) (e.g., 101) according to an embodiment of the present disclosure. FIG. 5 illustrates a timing diagram 500 of transmissions between the external activator device 201 and the IMD 101. The operations of FIG. 4 will be described in connection with FIG. 5.

The method 400 may be implemented as a software algorithm, package, or system that directs one or more hardware circuits or circuitry to perform the actions described herein. For example, the operations of the method 400 may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the device. At least one technical effect of at least one portion of the methods described herein includes i) receiving a connection request from an external activator device (e.g., 201) at an IMD (e.g., 101), ii) establishing a communication link (e.g., 104) between the external activator device and the IMD based on one or more communication link parameters, and iii) identifying the complete dataset of recorded transient data of interest to transfer from a temporary memory section (e.g., 699) to a long-term memory section (e.g., 698).

Beginning at 401, a patient activates the application on the external activator device 201. The patient may activate the application using numerous methods. For example, the patient may activate the application through a touch icon on the device screen. Alternatively or additionally, the application may be activated by the patient speaking to a voice recognition application. Alternatively or additionally, the patient may shake and/or move the device in certain ways to activate the application. Alternatively or additionally, the patient may use a touch function key on a computer, or a touch button icon on a smart watch and/or user wearable electronic accessory such as a Fitbit device to activate the application. The application may be activated by other methods as well.

At 402, the application on the external activator device 201 records a start-point. The start-point identifies the moment at which the patient activates the application. The start-point may also be referred to as a trigger time stamp. At the moment of activation, a timer on the external activator device 201 begins. The timer will continue to run until the communication link is established.

At 403, the CPU 302 instructs the RF subsystem 330 of the external activator device 201 to perform a scanning operation over an advertisement channel (e.g., 2402 MHz, 2426 MHz, 2480 MHz), for example, every 1 second. The output of the RF subsystem 330 corresponds to a scanning interval 503. The RF subsystem repeats the scanning interval 503 every scan period 501 such that the scanning interval 503 may be repeated, for example, every 4 seconds. The scanning interval 503 and/or scan period 501 may be longer or shorter than the above example. Additionally or alternatively, the scanning interval 503 and/or scan period 501 may be a predetermined length stored on the ROM 304, the RAM 306, or the hard drive 308. Optionally, the scanning interval 503 and/or scan period 501 is configured by the user, such that, the scanning interval 503 or scan period 501 may be increased or decreased. The RF subsystem 330 continually repeats the scanning interval 503 until the CPU 302 acknowledges receipt of an advertisement notice 505.

As one example, the IMD 101 and the external activator device 201 use a wireless protocol having a connection establishment delay (e.g., Bluetooth low energy) that utilizes a predefined frequency for an advertisement channel. The IMD 101 transmits advertisement notices 505 on the advertisement channel in accordance with a select communication initialization mode. For example, the advertisement notice 505 may include pairing and/or bondable information (e.g., passkey seed information). Additionally or alternatively, the advertisement notice may contain frequency synchronization information utilized to form the communication link 104, address information of the IMD 101, address information of the external activator device 201, and the like. The advertisement notice 505 may be repeated, at a set or variable interval or advertisement period 502, until the communication link 104 is established. The advertisement period 502 represents the length of time between successive advertisement notices 505.

The advertisement period 502, for example, may be 5 seconds, 30-45 seconds, 2-5 minutes, and the like. Optionally, the advertisement period 502 may be longer or shorter. Optionally, the advertisement period 502 may be input by a user (e.g., physician using an external device). Additionally or alternatively, the advertisement period may be predetermined and stored in memory 694 of the IMD 101. To initiate a pairing operation, the external activator device 201 monitors the advertisement channel in search of an advertisement notice 505 from the associated IMD 101.

The scan period 501 and the advertisement period 502 occur independent and asynchronous with respect to one another, such that the advertisement notices 505 intermittently overlap the scan intervals at 504 and 506. Each period length is predetermined from distinct and separate sources. The scan period 501 is predetermined or configured by the protocol syntax stored in the memory 356 of the external activator device 201. Separately, the advertisement period 502 is predetermined by the protocol syntax stored in the memory 694 of the IMD 101. One of the scan period 501 and the advertisement period 502 may be altered, while, the length of the other period (e.g., advertisement period 502, scan period 501) remains constant.

Once the external activator device 201 receives the advertisement notice 505, in the form of a data packet transmitted from the IMD 101, the CPU 302 analyzes or compares the data packet with the protocol syntax stored on the ROM 304, the RAM 306, or the hard drive 308. The protocol syntax may include the structure of an advertisement notice (e.g., data packet specifications, appropriate number of bits, frequency, or the like) utilized by the wireless protocol. Optionally, the advertisement notice 505 may include a unique code designating the packet as an advertisement. By comparing the protocol syntax with the data packet, the CPU 302 determines whether the received data packet is an advertisement notice 505 using the wireless protocol of the external activator device 201. If the received data packet is determined not to be an advertisement notice, the external activator device 201 may continue scanning the advertisement channel.

At 404, when the CPU 302 determines that the data packet received by the RF circuit 354 is the advertisement notice 505 from the IMD 101 (having the proper syntax), the CPU 302 outputs a connection request (e.g., data packet) to be transmitted by the RF circuit 354 on a separate channel. The connection request may include one or more communication link parameters based on the wireless protocol enabling the IMD 101 to establish a communication link (e.g., 104) with the external activator device 201. The one or more communication link parameters may include a communication interval, frequency (e.g., data channel), address, timeout parameters, cyclic redundancy check, a data channel map, and/or the like.

The external activator device 201 may transmit the connection request along the separate channel in response to an advertisement notice 505 transmitted from the IMD 101. For example, the wireless protocol may operate within a frequency range of 2400-2500 MHz. The wireless protocol may subdivide the frequency range into RF channels with a channel bandwidth (e.g., 2 MHz). The RF channels are allocated into two channel types, a data channel and the advertising channel. The data channel is used for communication between connected devices. The advertising channel is used by devices to discover new devices, initiating a connection, and broadcasting data.

The CPU 302 constructs a data packet representing the connection request by adding packet frames to conform to the protocol such as the address of the IMD 101 and/or external activator device 201, error detection codes such as CRC, a payload, or the like. The payload may include connection instructions (e.g., frequency of the data channel for the communication link 104) from the user intended for the IMD 101. Optionally, the data packet may include a static identification of the external activator device 201 and a dynamic seed. Once the data packet has been formed, the CPU 302 outputs the data packet to the RF subsystem 330 to be transmitted along the data channel to the IMD 101.

The RF circuit 610 receives the data packet and outputs to the microcontroller 660. The microcontroller 660 may store the data packet in memory 694 for analysis. The microcontroller 660 determines whether the data packet is in response to the advertisement notice 505 by comparing the address information of the data packet with the address transmitted by the IMD 101 within the advertisement notice 505. If the address information matches, the microcontroller 660 partitions the payload from the data packet.

When the select communication initialization mode corresponds to re-establishing a communication link with a previously paired and/or bonded external activator device 201, the microcontroller 660 may compare the address information of the external activator device 201 on the data packet with a previously paired and/or bonded links table stored in memory 694. The previously paired and/or bonded links table may be used to determine whether the IMD 101 has previously paired and/or bonded with the external activator device 201. For example, if the IMD 101 determines that the external activator device 201 corresponds to an un-paired and/or un-bonded external device (e.g., not previously paired) the IMD 101 may ignore the connection request from the external activator device 201. In another example, if the IMD 101 determines that the external activator device 201 was paired or bonded previously may partition the payload of the data packet. Once the microcontroller 660 identifies the connection request, the microcontroller 660 may instruct the RF circuit 610 to monitor the data channel identified in the connection request for further instructions from the external activator device 201, establishing the communication link 104.

During the select communication initialization mode corresponding to the predefined pairing and/or bonding procedure, the IMD 101 may determine when a connection request is received from external activator device 201 in connection with the select communication initialization mode (e.g., the predefined pairing and/or bonding procedure) by comparing the instructions (e.g., a connection request) from the payload to a stored instruction set on the memory 694 for the wireless protocol. In response to the connection request, the IMD 101 may be programmed and/or configured to transmit passkey seed information to the external activator device 201 when the connection request is received by the IMD 101 through a dedicated data channel. The passkey seed information may be transmitted between the IMD 101 and the external activator device 201 in accordance with a bonding procedure sequence of the wireless protocol. The bonding procedure may continue until the communication link 104 is established. See for example, U.S. Pat. No. 9,289,614, System and method for communicating with an implantable medical device, which is hereby incorporated by reference.

At 406, once the bonding procedure sequences complete, the communication link 104 between the external activator device 201 and the IMD 101 is fully formed and encrypted based on the one or more communication link parameters. At 408, once the communication link 104 is established, the application on the external activator device 201 records a stop-point. The stop-point identifies the moment at which the communication link 104 is established. The stop-point may also be referred to as a connection time stamp. At the moment communication connection is established, the timer on the external activator device 201 stops.

At 410 the application calculates the length of time between the trigger time stamp (e.g., the start-point) and the connection time stamp (e.g., the stop-point). An elapsed time delay occurs between when the patient activates the application on the external activator device 201 and the external activator device 201 establishes the communication link 104 with the IMD 101. The calculated length of time is an elapsed time value that corresponds to the elapsed time delay. Optionally, the elapsed time delay may be referred to as a connection establishment delay.

At 412, the external activator device 201 communicates to the IMD 101 the elapsed time value. The elapsed time value identifies a length of time corresponding to recorded exposed transient data temporarily stored on the temporary memory section 699 that is to be transferred to the long-term memory 698. The identification of transient data of interest is explained in more detail in FIG. 7.

Figure 7:
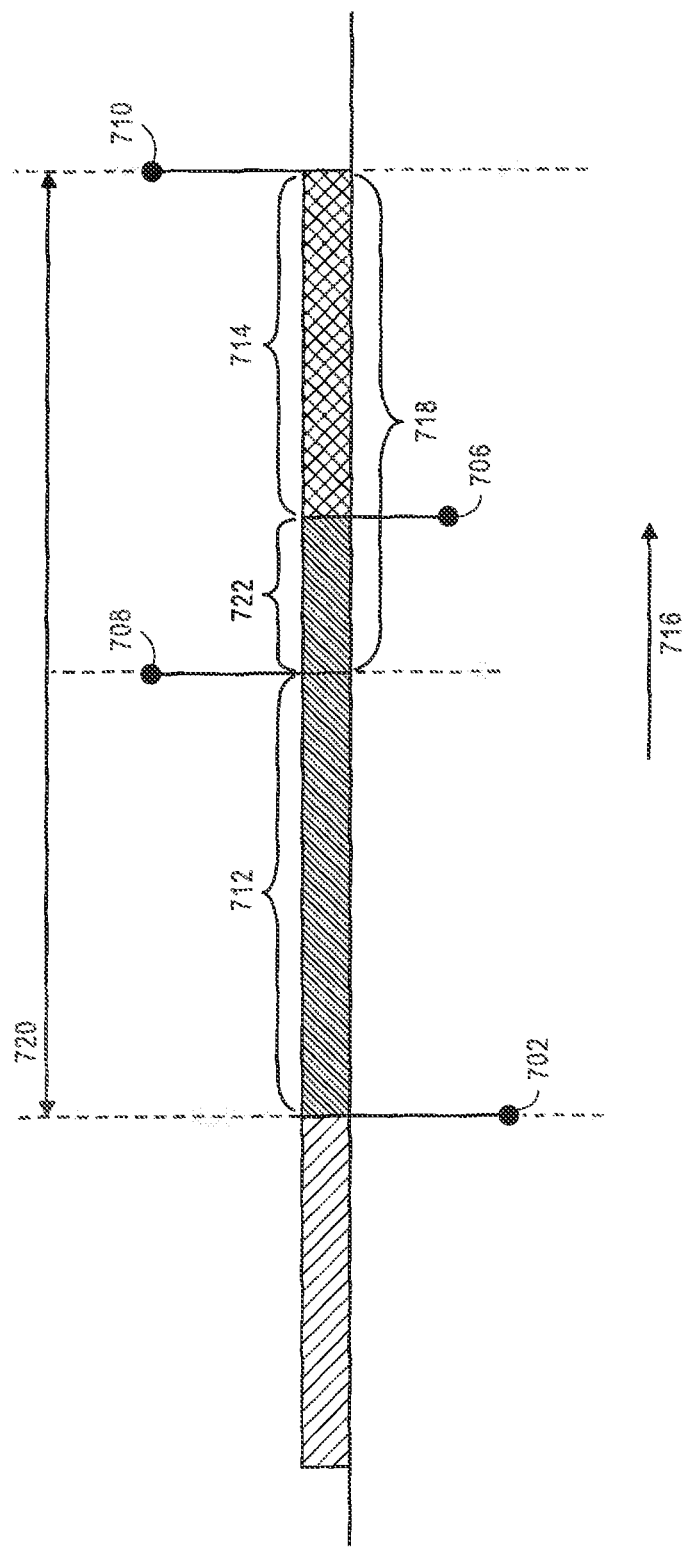
FIG. 7 illustrates a timing diagram of delays between communication activation between the external device and an implantable medical device according to an embodiment of the present disclosure.

FIG. 7 illustrates a buffer timeline 700 used to identify transient data temporarily stored in the temporary memory section 699 that is to be transferred to the long-term memory section 698. The buffer timeline 700 identifies specific points along the timeline used to identify the transient data of interest. A horizontal arrow 716 represents the progression of time of the buffer timeline 700. The temporary memory section 699 of the IMD 101 operates as a continuous buffer by recording transient data and temporarily storing the transient data for a predetermined length of time. The temporary storage of transient data continues as a repeating cyclical pattern. For example, the temporary memory section 699 may be configured to store a transient data corresponding to a limited length of time (e.g., up to 30 minutes). Once the temporary memory section 699 is full, new transient data is recorded by overwriting the oldest transient data of the temporary memory section 699. For example, the temporary memory section 699 may represent a first-in-first-out (FIFO) buffer. Over the course of the repeating temporary storage cycle, a period of time may be identified where the recorded transient data corresponding to the identified period of time is to transferred and stored in the long-term memory 698 as persistent data.

As the temporary memory section 699 of the IMD 101 continuously and cyclically records and temporarily stores transient data, the patient 106 may experience a symptom. For example, the symptom may be fainting, a fast heartbeat, heart flutter, dizziness, chest pain, and the like. The moment of time at which the patient experiences the symptom is identified as a symptom point 708 on the buffer timeline 700. The temporarily recorded transient data corresponding to the period of time the patient experiences the symptom may be physiologic data of interest.

Using the application on the external activator device 201, the patient initiates a patient activated (PA) storage request. The PA storage request triggers the external activator device 201 to begin scanning the advertisement channel for advertisement notices from the IMD 101 until the communication link 104 is established. For example, a patient may experience a fast heartbeat. The patient may want to store the physiologic data, corresponding to the time at which the fast heartbeat was experienced, in the long-term memory section 698 of the IMD 101. Using a smartphone, the patient may open the application on the smartphone and instruct the application to communicate to the IMD to begin identifying physiologic data. The PA storage request marks a trigger time stamp 706 at a point along the buffer timeline 700. The trigger time stamp 706 identifies a start point and starts a running clock on the external activator device 201.

However, a patient activation delay 722 occurs between the point in time the patient experiences the symptom and the point in time when the PA storage request is sent. The patient activation delay 722 corresponds to the length of time between the symptom point 708 and the trigger time stamp 706 along the buffer timeline 700. For example, when a patient feels a symptom, it might take some time to retrieve the smartphone, open the application, and send the PA storage request.

The patient activation delay 722 may be a predetermined value that is configured by the user, the physician, or the like. The patient activation delay 722 may be stored on the external activator device 201 and may be communicated to the IMD 101. For example, the patient activation delay 722 may be a 2-minute length of time. The patient activation delay 722 represents a length of time corresponding to transient data of interest. The transient data corresponding to the patient activation delay 722 may be referred to as activation transient data. The activation transient data may be identified to be transferred from the temporary memory section 699 to the long-term memory section 698. The external activator device 201 may communicate the value corresponding to the patient activation delay 722 to the IMD 101.

Optionally, the patient activation delay 722 may be a predetermined value configured by the user, the physician, or the like, that corresponds to a symptom the patient has selected. A patient activation delay 722 value may be assigned to each symptom. A unique patient activation delay value may be assigned to each unique symptom that is independent of the patient activation delay value that may be assigned to a different symptom. Optionally, a common patient activation delay value may be assigned to multiple symptoms. For example, the patient activation delay value assigned to fainting may be 20 minutes, and a patient activation delay value assigned to a fast heartbeat may be 5 minutes. The patient activation delay value for fainting may be predetermined to account for the time when the patient has fainted and is unable to operate the external activator device 201. For example, when a patient has fainted, the patient may be unconscious for a period of time. When the patient comes to, the patient may activate the application on a smartphone to record the transient data surrounding the moment in time the patient has fainted. In order to identify the length of time the patient was unconscious, the patient activation delay value assigned to fainting may be an excessive value.

Once the communication link 104 is established between the devices 101 and 201, the PA storage request is communicated to the IMD 101. At the moment the communication link 104 is established, the application marks the buffer timeline 700 with a connection time stamp 710 and the running clock on the external activator device 201 stops. As previously detailed, an elapsed time delay 714 occurs between when the patient activates the application on the external activator device 201 and the communication link 104 is established between the external activator device 201 and the IMD 101. The elapsed time delay 714 corresponds to the length of time between the trigger time stamp 706 (e.g., the start-point) and the connection time stamp 710 (e.g., the stop-point). The elapsed time delay 714 represents a length of time corresponding to transient data of interest. The transient data corresponding to the elapsed time delay 714 may be referred to as delayed transient data. The delayed transient data may be identified to be transferred from the temporary memory section 699 to the long-term memory section 698.

The external activator device 201 may determine a total activation value 718. The total activation valued 718 comprises the elapsed time delay 714 and patient activation delay 722. The total activation value 718 identifies a length of time corresponding to transient data of interest. The external activator device 201 may communicate the total activation value 718 to the IMD 101.

As the external activator device 201 connects with the IMD 101, the application may display to the patient 106 on the external activator device 201 a list of symptoms. As previously detailed, the list of symptoms may be a predetermined list configured by a physician of identifiable symptoms the patient may experience and related to the health of the patient. For example, the list of symptoms may include fainting, fast heartbeat, heart flutter, dizziness, chest pain, and the like. A symptom time value 712 may be assigned to each symptom of the predetermined list of symptoms. A unique symptom time value may be assigned to each unique symptom that is independent of the symptom time value that may be assigned to a different symptom. Optionally, a common symptom time value may be assigned to multiple symptoms on the list of symptoms. For example, a symptom time value assigned to fainting may be 20 minutes, and a symptom time value assigned to fast heartbeat may be 16 minutes. The symptom time value 712 may be a predetermined length of time configured by a physician, or the like. The symptom time value 712 represents a length of time corresponding to transient data of interest. The transient data corresponding to the symptom time value 712 may be referred to as symptom transient data. The symptom transient data may be identified to be transferred from the temporary memory section 699 to the long-term memory section 698.

Using the application, the patient 106 may select the symptom presently experienced from the list of symptoms displayed by the application on the external activator device 201. The external activator device 201 may communicate the selected symptom and the corresponding symptom time value 712 to the IMD 101.

The external activator device 201 has communicated a total time value 720 to the IMD 101. The total time value 720 identifies a length of time corresponding to the complete set of transient data of interest that is to be transferred from the temporary memory section 699 to the long-term memory section 698. The total time value 720 comprises the summation of the symptom time value 712, and the total activation value 718.

Figure 8:
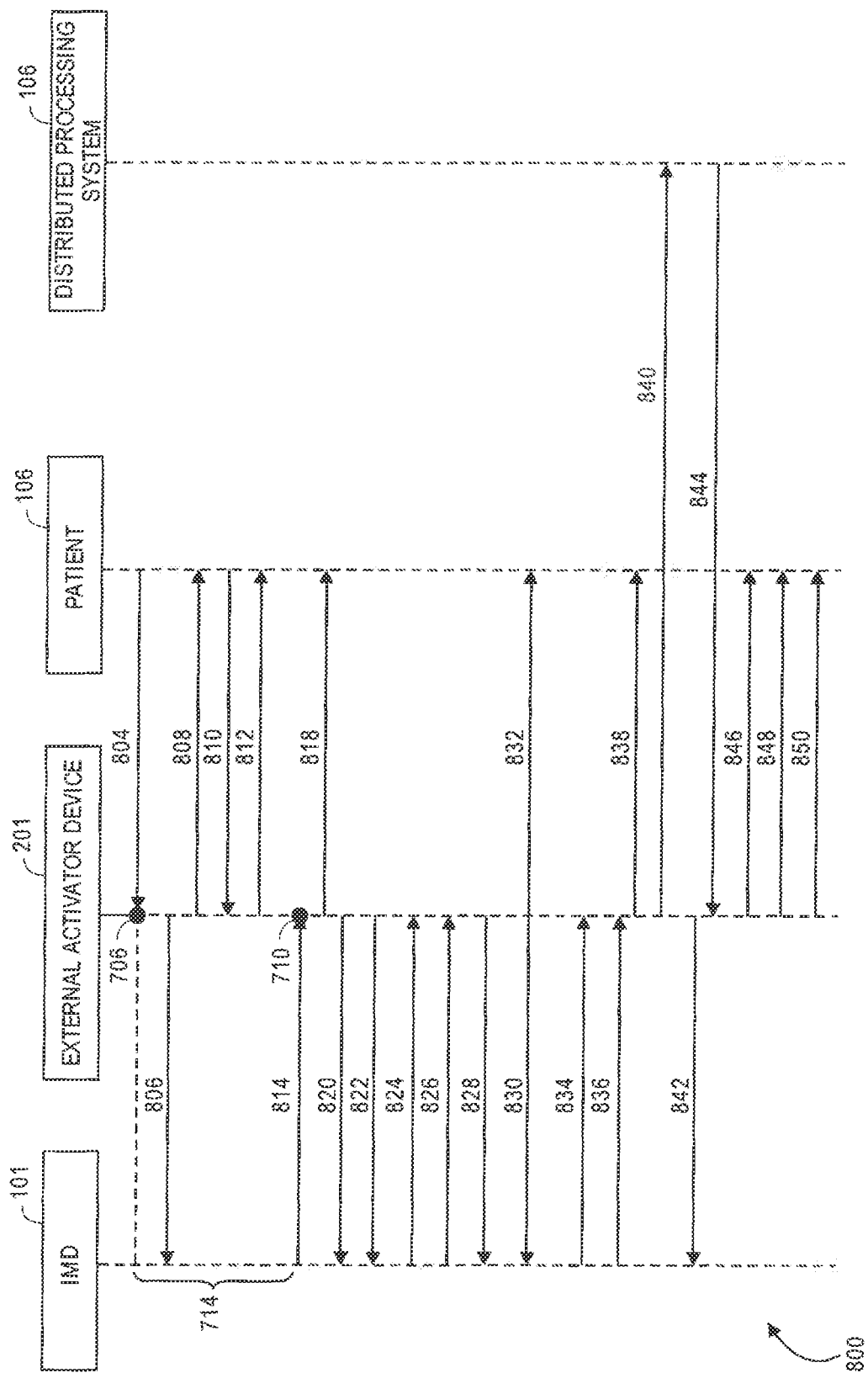
FIG. 8 illustrates a message sequence between an external device, an implantable medical device, and a user according to an embodiment of the present disclosure.

FIG. 8 illustrates a message sequence 800 between the application on the external activator device 201, the IMD 101, the patient 106, and a distributed processing system 900. A vertical arrow 852 represents the progression of time of the message sequence 800.

At 804 the patient 106 initiates a PA storage request with the application on the external activator device 201. The application on the external activator device 201 identifies and records the trigger time stamp 706. For example, the patient may identify they are experiencing a heart flutter. Using a smartphone, the patient may open the application and activate a storage request to be communicated to the IMD. At 806, the external activator device 201, in response, begins scanning the advertising channel for an advertising notice from the IMD 101 in order to establish a communication link. While the external activator device 201 is connecting to the IMD 101, at 808 the application displays a list of symptoms to the patient. As previously discussed, the list of symptoms may be a predetermined list of symptoms configured by a physician or the like. At 810 the patient selects the symptom identifying the current state of health of the patient. For example, the patient may identify they are experiencing a heart flutter. Using a smartphone, the patient selects the heart flutter symptom from the list of symptoms. At 812, the application displays to the patient that the external activator device 201 is in the process of establishing a communication link with the IMD 101.

At 814, the IMD 101 communicates to the external activator device 201 that the communication link 104 has been established. The application on the external activator device 201 identifies and records the connection time stamp 710. The external activator device may now communicate with the IMD 101 across the communication link 104. The application may calculate the elapsed time delay value corresponding to the elapsed time delay 714. The elapsed time delay 714 corresponds to the length of time between the trigger time stamp 706 and the connection time stamp 710.

At 818, the application may display to the patient that the communication link 104 has been established, and that the IMD 101 may be recording transient data.

At 820, the external activator device 201 communicates to the IMD 101 the total activation value 718 (corresponding to FIG. 7). The total activation value 718 corresponds to the delay between the patient experiencing a symptom and the external activator device establishing the communication link 104 with the IMD 101. The total activation value 718 is a length of time corresponding to transient data of interest that is to be transferred from the temporary memory section 699 to the long-term memory section 698. The total activation value 718 comprises the elapsed time delay 714 and the patient activation delay 722. For example, the patient may experience a heart flutter. The application, using a timer on the external activator device, calculates a 3-minute delay that occurs between the patient sending a PA storage request (e.g., the trigger time stamp 706) and the external activator device establishing a communication link with the IMD (e.g., the connection time stamp 710). The 3-minute delay identifies the elapsed time delay 714. Additionally, the external activator device 201 comprises a predetermined 4 minute value identified as the patient activation delay 722. The external activator device 201 communicates the 7 minute total activation value 718 to the IMD 101.

At 822 the external activator device 201 communicates a message to the IMD 101 to transfer the transient data corresponding to the total activation value 718 to the long-term memory section 698 for storage. The IMD 101 may communicate to the external activator device at 824 when the transfer of data begins, and at 826 when the transfer of data is complete.

At 828, the external activator device 201 communicates to the IMD 101 the symptom that the patient previously selected at 810, and the corresponding symptom time value. For example, the patient has, using the application on the smartphone, identified the symptom to be a heart flutter. The application has a predetermined symptom time value of 13-minutes assigned to the heart flutter symptom. The external activator device 201 communicates to the IMD 101 the heart flutter symptom and the 13-minute symptom time value.

At 830, the external activator device 201 communicates a request to the IMD 101 to transmit the transient data corresponding to the total time value 720 (corresponding to FIG. 7) from the long-term memory section 698 to the external activator device 201. For example, the transient data may be transmitted to the external activator device in order to upload to a database where the physician may upload and/or download the transient data to review. The application on the external activator device 201 displays the status of the data transmission to the patient at 832. At 834, the IMD communicates to the external activator device that the transmission of data is in process, and at 836 the IMD communicates that the transmission of data is complete. Once the transmission of data from the long-term memory section 698 of the IMD 101 to the external activator device 201 is complete, the application displays to the patient a completion notification at 838. At 842 the external activator device 201 disables the communication link 104 with the IMD 101 once the transient data transmission from the IMD to the external activator device is complete.

Figure 9:
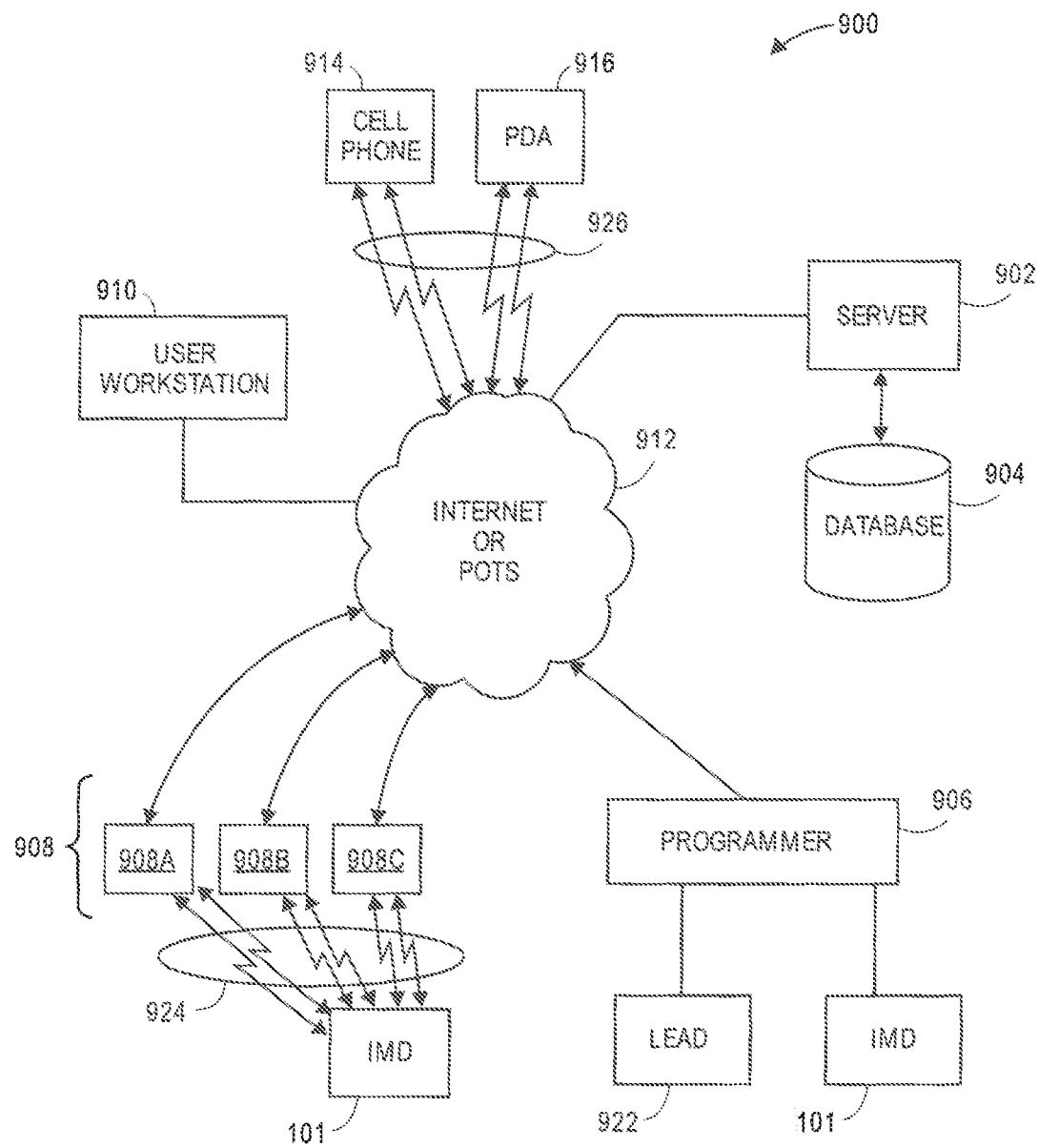
FIG. 9 illustrates a distributed processing system according to an embodiment of the present disclosure.

FIG. 9 illustrates the distributed processing system 900 in accordance with one embodiment. The distributed processing system 900 includes a server 902 connected to a database 904, a programmer 906, at least one of a local RF transceiver 908 and a user workstation 910 electrically connected to a communication system 912. The local RF transceiver 908 may be at least one of an external device (corresponding to the external activator device 201 of various embodiments). For example, the local RF transceiver 908 may be a tablet computer 908*a*, a smartphone 908*b*, a laptop computer 908*c*, and the like.

The communication system 912 may be the internet, a voice over IP (VoIP) gateway, a local plain old telephone service (POTS) such as a public switched telephone network (PSTN), a cellular phone based network, and the like. Alternatively, the communication system 912 may be a local area network (LAN), a campus area network (CAN), a metropolitan area network (MAN), or a wide area network (WAM). The communication system 912 serves to provide a network that facilitates the transfer/receipt of information such as cardiac signal waveforms, ventricular and atrial heart rates.

The server 902 is a computer system that provides services to other computing systems over a computer network. The server 902 controls the communication of information such as cardiac signal waveforms, ventricular and atrial heart rates, and detection thresholds. The server 902 interfaces with the communication system 912 to transfer information between the programmer 906, the local RF transceiver 908, the user workstation 910 as well as a cell phone 914 and a personal data assistant (PDA) 916 to the database 904 for storage/retrieval of records of information. On the other hand, the server 902 may upload raw transient signals from an implanted lead 922 or the IMD 101 via the local RF transceiver 908 or the programmer 906.

The database 904 stores information such as cardiac signal waveforms, ventricular and atrial heart rates, and the like, for a single or multiple patients. The information is downloaded into the database 904 via the server 902 or, alternatively, the information is uploaded to the server from the database 904. The programmer 906 is similar to the external activator device 201 and may reside in a patient's home, a hospital, or a physician's office. The programmer 906 interfaces with the lead 922 and the IMD 101. The programmer 906 may wirelessly communicate with the IMD 101 and utilize protocols, such as Bluetooth, Bluetooth Low Energy (BLE), GSM, infrared wireless LANs, HIPERLAN, 3G, satellite, as well as circuit and packet data protocols, and the like. Alternatively, a hard-wired connection may be used to connect the programmer 906 to the IMD 101. The programmer 906 is able to acquire cardiac signals from the surface of a person (e.g., ECGs), intra-cardiac electrogram (e.g., IEGM) signals from the IMD 101, and/or cardiac signal waveforms, ventricular and atrial heart rates, and detection thresholds from the IMD 101. The programmer 906 interfaces with the communication system 912, either via the internet or via POTS, to upload the information acquired from the lead 922 or the IMD 101 to the server 902.

The local RF transceiver 908 interfaces with the communication system 912 to upload one or more of transient data sets such as cardiac signal waveforms, ventricular and atrial heart rates, and detection thresholds to the server 902. In one embodiment, the IMD 101 has a bi-directional connection 924 with the local RF transceiver 908 via a wireless connection. The local RF transceiver 908 is able to acquire cardiac signals from the surface of a person, intra-cardiac electrogram signals from the IMD 101, and/or cardiac signal waveforms, ventricular and atrial heart rates, and detection thresholds from the IMD 101. On the other hand, the local RF transceiver 908 may download stored cardiac signal waveforms, ventricular and atrial heart rates, and detection thresholds, and the like, from the database 904 to the IMD 101.

The user workstation 910 may interface with the communication system 912 via the internet or POTS to download cardiac signal waveforms, ventricular and atrial heart rates, and detection thresholds via the server 902 from the database 904. Alternatively, the user workstation 910 may download raw data from the lead 922 or IMD 101 via either the programmer 906 or the local RF transceiver 908. Once the user workstation 910 has downloaded the cardiac signal waveforms, ventricular and atrial heart rates, or detection thresholds, the user workstation 910 may process the information in accordance with one or more of the operations described above. The user workstation 910 may download the information and notifications to the cell phone 914, the PDA 916, the local RF transceiver 908, the programmer 906, or to the server 902 to be stored on the database 904. For example, the user workstation 910 may communicate data to the cell phone 914 or PDA 916 via a wireless communication link 926.

Returning to FIG. 8, the transient data of interest has been transmitted from the long-term memory section 698 of the IMD 101 to the external activator device 201. At 840 the external activator device 201 (corresponding to the local RF transceiver 908 of FIG. 9) may upload the transmitted transient data of interest to the database 904 of the distributed processing system 900 of FIG. 9. The uploaded transient data may be available to be uploaded and/or downloaded by a physician from the database 904 using one of the cell phone 914, PDA 916, workstation 910, or the like, of FIG. 9.

At 844, the communication system 912 communicates to the external activator device 201 that the upload of transient data to the database 904 is complete. The application displays notification to the patient that the upload of data is complete at 846. At 848 the patient communicates to the application that no more action is to be taken, and at 850 the application returns to the home screen.

Figure 10:
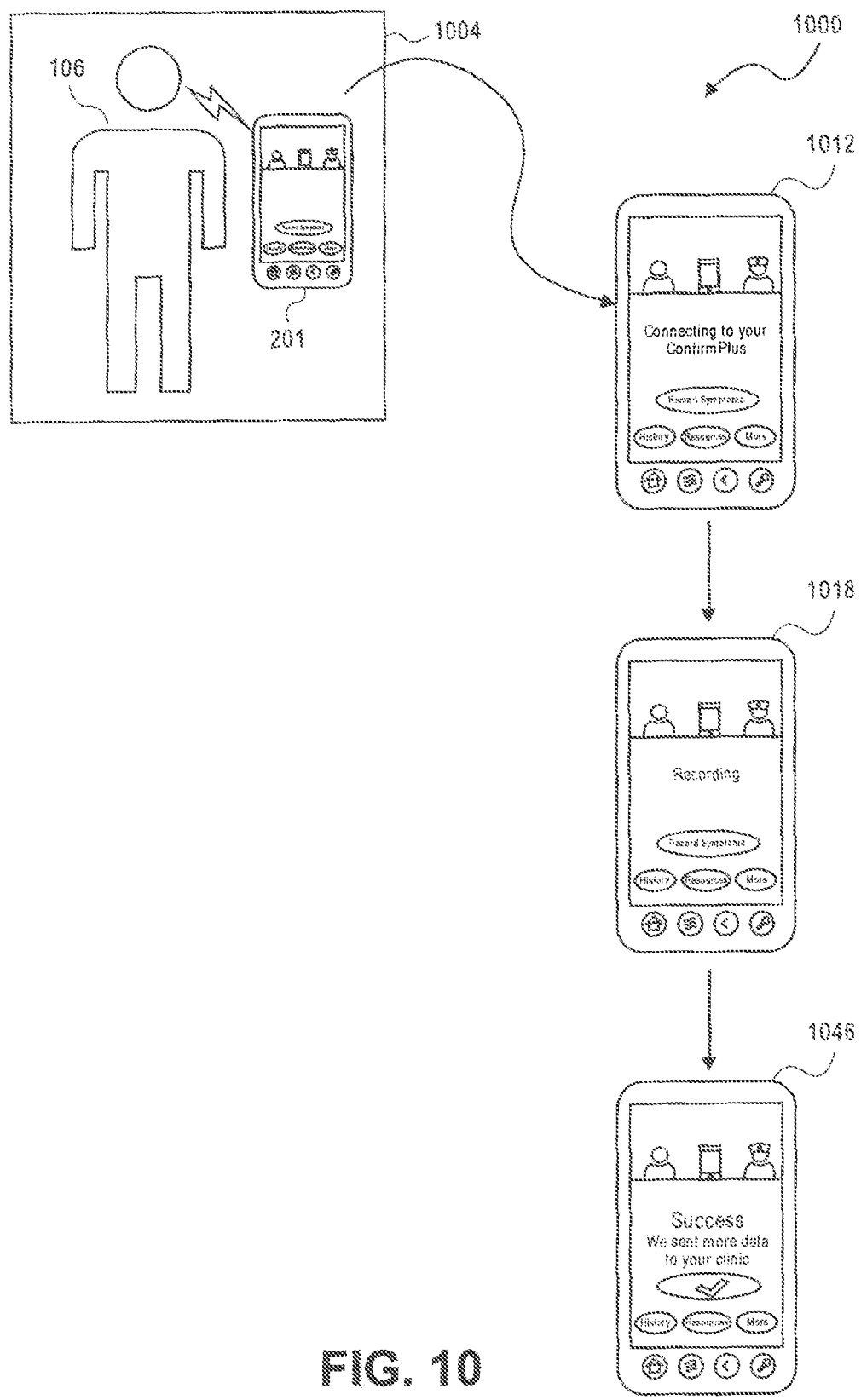
FIG. 10 illustrates a display sequence presented by an external device according to an embodiment of the present disclosure.

FIG. 10 illustrates a display sequence 1000 presented on a device in accordance with one embodiment. The patient 106 experiences a symptom. At 1004, the patient activates the application on the external activator device 201. The application on the external activator device 201 displays to the patient a connection screen 1012 (corresponding to 812 of FIG. 8). For example, the connection screen 1012 may communicate to the patient that the external activator device 201 is attempting to establish a communication link with the IMD 101. The application on the external activator device 201 displays to the patient a recording screen 1018 (corresponding to 818 of FIG. 8). For example, the recording screen may communicate to the patient that the external activator device 201 has connected with the IMD 101 and that transient data of interest is being recorded (e.g., transferred from the temporary memory section 199 to the long-term memory section 198). At 1046, the application displays to the patient that the transient data of interest has been successfully identified and transmitted to the database 904 (corresponding to 846 of FIG. 8). Alternatively or additionally, the application may display one or more display screens communicating the status of recording and/or transmitting transient data of interest. For example, the application may also communicate if an error occurs during the process. Optionally, other display screens may be used to communicate additional information to the patient.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. An implantable medical device (IMD), comprising:
   means for collecting transient data utilizing an IMD;
   means for storing the transient data in a temporary memory section of the IMD device;
   means for receiving a patient activated (PA) storage request, the PA storage request including activation information related to a duration of time between entry of a patient designated trigger point and a connection event wherein the IMD establishes a communications link to an external activator device;
   means for transferring a segment of the transient data from the temporary memory section to a long-term memory, wherein the segment is based at least in part on the trigger point and the activation information; and
   means for analyzing the transient data to detect a condition experienced by the patient at the patient entered trigger point.

2. The device of claim 1, wherein the activation information includes an elapsed time corresponding to a duration of time between entry of the trigger point and issuance of the PA storage request by an external activation device.

3. The device of claim 1, wherein the activation information includes a patient condition indicator indicative of a condition experienced by the patient at the patient entered trigger point, the device further comprising means for storing the patient condition indicator with the segment of transient data.

4. The device of claim 1, further comprising receiving, as the trigger point, means for inputting by a user to an external activator device, the external activator device transmitting the PA storage request based on the input.

5. The device of claim 1, further comprising establishing a communications link between the IMD and an external activator device.

6. The device of claim 1, further comprising
   means for identifying a trigger time stamp corresponding to a point in time when the trigger point occurs;
   means for identifying a connection time stamp corresponding to a point in time when a communications link is established between the IMD and the external activator device; and
   means for calculating an elapsed time based on the trigger and connection time stamps, the elapsed time representing at least a portion of the activation information.

7. The device of claim 1, wherein the segment of the transient data includes a starting point corresponding to the point in time when the patient entered trigger point occurred.

8. The device of claim 1, further comprising means for establishing a communications session between the IMD and the external device, the communications session utilizing a wireless protocol having a connection establishment delay.

9. The device of claim 1, wherein the means for collecting includes means for collecting electrocardiogram (EGM) data as the transient data and the means for transferring includes means for copying EGM data from the temporary memory section to the long term memory.

10. The device of claim 7, further comprising means for transmitting the EGM data from the IMD to the external device.

11. An medical system, comprising:
   an input to collect transient data;
   a temporary memory configured to temporarily store the transient data;
   a long term memory configured to store data long term;
   an external activator configured to transmit a patient activated data storage request;
   a transceiver circuit configure to communicate wirelessly with the external activator and to receive the patient activated (PA) storage request, the PA storage request including activation information related to a patient designated trigger point and an elapsed time corresponding to a duration of time between entry of the trigger point and a connection event at which the IMD establishes a communications link to an external activator device; and
   a processor to transfer a segment of the transient data from the temporary memory to a long-term memory, wherein the segment is based at least in part on the trigger point and the active information.

12. The system of claim 11, further comprising one or more sensors connected to a sensing circuit to sense cardiac signals as the transient data.

13. An medical system, comprising:
   one or more electrodes connected to a sensing circuit to sense cardiac signals as transient data;
   a temporary memory configured to temporarily store transient data;
   a long term memory configured to store data long term;
   an external activator configured to transmit a patient activated data storage request;
   a transceiver circuit configure to communicate wirelessly with the external activator and to receive the patient activated (PA) storage request, the PA storage request including activation information related to a patient designated trigger point and an elapsed time corresponding to a duration of time between entry of the trigger point and a connection event at which the IMD establishes a communications link to an external activator device; and a processor to transfer a segment of the transient data from the temporary memory to a long-term memory, wherein the segment is based at least in part on the trigger point and the active information.

14. The device of claim 11, wherein the transceiver circuit is configured to establish a communications session between the IMD and the external activator utilizing a wireless protocol having a connection establishment delay.

15. The system of claim 11, wherein the transceiver circuit is configured to transmit the transient data from the IMD to the external activator.

16. An implantable medical device (IMD), comprising:
temporary memory configured to store transient data;
a transceiver circuit configured to receive a patient activated (PA) storage request wirelessly from an external device, the PA storage request including information indicative of an elapsed time delay for at least one of a reaction delay or a connection establishment delay; and
a processor configured to manage transfer of a segment of the transient data from the temporary memory section to a long-term memory, wherein the segment is based at least in part on at least one of the reaction delay or a connection establishment delay.

17. The IMD of claim 16, wherein at least one of i) the reaction delay corresponds to a time between when a user determines that a symptom is being experienced and the user enters a trigger on the external device or ii) the connection establishment delay corresponds a time between when a user enters a trigger on the external device and the external device establishes a communication session with the IMD.

18. The IMD of claim 16, wherein the segment of the transient data transferred to the long-term memory includes exposed transient data that represents a portion of the transient data that is written to the temporary memory for a period of time before the IMD receives the PA storage request.

19. The IMD of claim 18, wherein the exposed transient data begins at a time when a patient experiences a symptom and ends when the IMD receives the PA storage request.

20. The IMD of claim 18, wherein the exposed transient data begins at a predetermined time before or after a patient experiences a symptom and ends when the IMD receives the PA storage request.

21. The IMD of claim 16, further comprising memory configured to store a list of symptom time values assigned to corresponding patient symptoms, the PA storage request including an indication of a current patient symptom, wherein the processor is configured to adjust a length of time corresponding to the segment of the transient data based on a one of the symptom time values associated with the current patient symptom.

22. A medical system, comprising:
a temporary memory configured to temporarily store transient data;
a long term memory configured to store data long term;
an external patient activator configured to transmit a patient activated data storage request;
a transceiver circuit configured to receive a patient activated (PA) storage request wirelessly from an external device, the PA storage request including information indicative of an elapsed time delay for at least one of a reaction delay or a connection establishment delay; and
a first processor configured to manage transfer of a segment of the transient data from the temporary memory section to a long-term memory, wherein the segment is based at least in part on at least one of the reaction delay or a connection establishment delay.

23. The system of claim 22, wherein at least one of i) the reaction delay corresponds to a time between when a user determines that a symptom is being experienced and the user enters a trigger on the external device or ii) the connection establishment delay corresponds a time between when a user enters a trigger on the external device and the external device establishes a communication session with the IMD.

24. The system of claim 22, wherein the segment of the transient data transferred to the long-term memory includes exposed transient data that represents a portion of the transient data that is written to the temporary memory for a period of time before the IMD receives the PA storage request.

25. The system of claim 24, wherein the exposed transient data begins at a time when a patient experiences a symptom and ends when the IMD receives the PA storage request.

26. The system of claim 22, further comprising memory configured to store a list of symptom time values assigned to corresponding patient symptoms, the PA storage request including an indication of a current patient symptom, wherein the processor is configured to adjust a length of time corresponding to the segment of the transient data based on a one of the symptom time values associated with the current patient symptom.

27. The system of claim 22, wherein the external patient activator comprises memory configured to store program instructions and a second processor that, when executing the program instructions, identifies a trigger point in response to a user input and wirelessly transmits the PA storage request based on the user input, the system further comprising an implantable medical device (IMD) that comprises the temporary memory, transceiver circuit and first processor.

28. The system of claim 27, wherein the long-term memory is provided in at least one of the external patient activator or the IMD.

* * * * *